(12) United States Patent
Kaushikkar et al.

(10) Patent No.: US 6,965,704 B2
(45) Date of Patent: Nov. 15, 2005

(54) SYSTEM, METHOD, AND COMPUTER SOFTWARE PRODUCT FOR GRID ALIGNMENT OF MULTIPLE SCANNED IMAGES

(75) Inventors: Shantanu V. Kaushikkar, San Jose, CA (US); Sangita B. Patil, Santa Clara, CA (US)

(73) Assignee: Affymetrix, Inc., Santa Clara, CA (US)

( * ) Notice: Subject to any disclaimer, the term of this patent is extended or adjusted under 35 U.S.C. 154(b) by 522 days.

(21) Appl. No.: 09/682,076

(22) Filed: Jul. 17, 2001

(65) Prior Publication Data

US 2002/0025082 A1 Feb. 28, 2002

Related U.S. Application Data

(60) Provisional application No. 60/286,578, filed on Apr. 26, 2001, provisional application No. 60/242,973, filed on Oct. 24, 2000, provisional application No. 60/226,999, filed on Aug. 22, 2000.

(51) Int. Cl.[7] .............................................. G06K 9/32
(52) U.S. Cl. ..................................... 382/294; 382/129
(58) Field of Search ................................ 382/129, 294

(56) References Cited

U.S. PATENT DOCUMENTS

| | | | |
|---|---|---|---|
| 5,604,819 A | * | 2/1997 | Barnard ....................... 382/151 |
| 5,631,734 A | | 5/1997 | Stern et al. |
| 5,807,522 A | | 9/1998 | Brown et al. |
| 5,916,747 A | * | 6/1999 | Gilchrist et al. ............... 435/6 |
| 6,040,193 A | | 3/2000 | Winkler et al. |
| 6,090,555 A | | 7/2000 | Fiekowsky et al. |
| 6,110,426 A | | 8/2000 | Shalon et al. |
| 6,157,700 A | * | 12/2000 | Sako ........................ 378/98.12 |
| 6,309,822 B1 | | 10/2001 | Fodor et al. |
| 6,345,115 B1 | * | 2/2002 | Ramm et al. ............... 382/133 |
| 6,349,144 B1 | | 2/2002 | Shams |
| 6,562,565 B1 | | 5/2003 | Pinkel et al. |
| 6,591,196 B1 | | 7/2003 | Yakhini et al. |
| 2002/0047853 A1 | | 4/2002 | Bartell |

OTHER PUBLICATIONS

Axon Instruments, Inc. Press Release dated Mar. 8, 2000 entitled, "Axon Instruments Announces Release of GenePix Pro 3.0", http://www.axon.com/press/pr20000308.htm.
GenePix Pro 3.0 Software, http://www.apbiotech.com/application/miroarray/GenePix_Pro3.htm.
GenePix Pro Features, pp. 1-19.

* cited by examiner

Primary Examiner—Andrew W. Johns
Assistant Examiner—Patrick Edwards
(74) Attorney, Agent, or Firm—William R. McCarthy, III; Philip L. McGarrigle; Alan B. Sherr

(57) ABSTRACT

Systems, methods, and computer program products are described for aligning multiple images of arrays of biological materials. One method includes aligning a grid with a first image, generating grid alignment data based on the alignment of the grid with the first image, storing the grid alignment data in memory, retrieving the grid alignment data responsive to an indication to align a second image, and analyzing the second image based on the retrieved grid alignment data. In some implementations, the first image and second images are generated by scanning the same array of biological materials. The array may be a spotted array, a synthesized array, or other type of parallel biological assay.

31 Claims, 12 Drawing Sheets

SYSTEM, METHOD, AND COMPUTER SOFTWARE PRODUCT FOR GRID ALIGNMENT OF MULTIPLE SCANNED IMAGES

CROSS REFERENCE TO RELATED APPLICATIONS

The present application relates to and claims priority from U.S. Provisional Patent Application Ser. No. 60/226,999, titled "System, Method, and Product for Linked Window Interface," filed Aug. 22, 2000; U.S. Provisional Patent Application Ser. No. 60/242,973, titled "System, Method, and Product for Scanned Image Alignment," filed Oct. 24, 2000; and U.S. Provisional Patent Application Ser. No. 60/286,578, titled "System, Method, and Product for Scanning of Biological Materials," filed Apr. 26, 2001, which are hereby incorporated herein by reference in their entireties for all purposes. The present application also relates to U.S. patent application Ser. No. 09/682,071, entitled "System, Method, and Computer Program Product for Gain Adjustment in Biological Microarray Scanner," and to U.S. patent application Ser. No. 09/682,074, entitled "System, Method, and Computer Software Product for Specifying a Scanning Area of a Substrate," both of which are filed concurrently herewith and are hereby incorporated herein by reference in their entireties for all purposes.

COPYRIGHT STATEMENT

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

BACKGROUND OF INVENTION

1. Field of the Invention

The present invention relates to computer systems, methods, and products for analyzing images and, more particularly, for placing alignment grids on scanned images of high-density arrays of biological materials.

2. Related Art

Synthesized probe arrays, such as Affymetrix® GeneChip® arrays, have been used to generate unprecedented amounts of information about biological systems. For example, a commercially available GeneChip® array set from Affymetrix, Inc. of Santa Clara, Calif., is capable of monitoring the expression levels of approximately 6,500 murine genes and expressed sequence tags (EST's). Experimenters can quickly design follow-on experiments with respect to genes, EST's, or other biological materials of interest by, for example, producing in their own laboratories microscope slides containing dense arrays of probes using the Affymetrix® 417™ Arrayer or other spotting devices.

Analysis of data from experiments with synthesized and/or spotted probe arrays may lead to the development of new drugs and new diagnostic tools. In some conventional applications, this analysis begins with the capture of fluorescent signals indicating hybridization of labeled target samples with probes on synthesized or spotted probe arrays. The devices used to capture these signals often are referred to as scanners, an example of which is the Affymetrix® 428™ Scanner from Affymetrix, Inc. of Santa Clara, Calif.

There is a great demand in the art for methods for organizing, accessing and analyzing the vast amount of information collected by scanning microarrays. Computer-based systems and methods have been developed to assist a user to obtain and visualize the vast amounts of information generated by the scanners. These commercial and academic software applications typically provide such information as intensities of hybridization reactions or comparisons of hybridization reactions. This information may be displayed to a user in graphical form.

SUMMARY OF INVENTION

In accordance with some embodiments of the present invention, methods are described that include (a) aligning a grid with a first image; (b) generating grid alignment data based on the alignment of the grid with the first image; (c) storing the grid alignment data in memory; (d) retrieving the grid alignment data responsive to an indication to align a second image; and (e) analyzing the second image based on the retrieved grid alignment data. In some implementations of these methods, the first and second images are generated by scanning a same probe array. For example, the first image may be generated by scanning the probe array with a first excitation beam having a first wavelength; and the second image may be generated by scanning the probe array with a second excitation beam having a second, different, wavelength. The probe array may be a spotted array, synthesized array, or other type of parallel biological assay. The grid alignment data may be applied to multiple images in addition to the second image. For example, a user may specify that a probe array is to be scanned to provide N images. The grid alignment data is generated based on the alignment of a grid with a first of the N images, and this grid alignment data is applied to each of the other N images.

One advantage of this method in some embodiments is that grid alignment need not (although it may) be performed on images other than the first image. Also, grids need not (but may) be displayed for those other images. Rather, in some implementations, alignment data based on aligning a grid with a first image is stored and may be retrieved and applied to other images. This application to other images thus, in some aspects of these implementations, may take place without user involvement, or merely in accordance with a user indication to analyze the other images.

In some implementations, the methods may further include (f) receiving one or more user-selected grid aligning parameters. The user-selected grid aligning parameters may include a fixed algorithm shape with easy threshold, a fixed algorithm shape with tight threshold, a variable algorithm shape with easy threshold, a variable algorithm shape with tight threshold, an estimated feature size, and/or any combination thereof. The estimated feature size may be based on a dimension of a depositing element.

Some implementations of these methods include receiving a user selection of a number of images to scan and scanning the user-selected number of images. Also, the method may include receiving a user selection of one or more parameters for scanning, such as a gain for one or more of the user-selected number of images, and/or an indicator of an excitation source for one or more of the user-selected number of images.

In accordance with other embodiments, a computer program product is described that includes a grid aligner that aligns a grid with a first image. The product also has an image analysis manager that has an image analyzer, an image analysis data storer, and a multiple scan alignment controller. The image analyzer generates grid alignment data based on the alignment of the grid with the first image. The image analysis data storer stores the grid alignment data in memory. The multiple scan alignment controller retrieves the grid alignment data responsive to an indication to analyze (or align) a second image. The image analyzer analyzes the second image based on the retrieved grid alignment data. This analysis typically involves identification and categorization of pixels for analysis based on the grid alignment data. In this sense, it may be said that the image analyzer applies a grid (based on analysis of the first image) to other images. The computer program product may also have a GUI manager that receives one or more user-selected grid aligning parameters.

In accordance with yet other embodiments, a scanning system is described that includes a scanner and a compute program product. The scanner scans a first probe array to generate first and second (or more) images. The computer program product includes a grid aligner that aligns a grid with the first image, and an image analysis manager. The image analysis manager has an image analyzer that generates grid alignment data based on the alignment of the grid with the first image, an image analysis data storer that stores the grid alignment data in memory, and a multiple scan alignment controller that retrieves the grid alignment data responsive to an indication to align the second image. The image analyzer analyzes the second image based on the retrieved grid alignment data.

Also described are embodiments of a scanning system that includes a scanner, a computer, and a computer program product. The scanner scans a probe array to generate first and second (or more) images. The computer program product, when executed on the computer, performs a method including aligning a grid with the first image, generating grid alignment data based on the alignment of the grid with the first image, storing the grid alignment data in memory, retrieving the grid alignment data responsive to an indication to align the second image, and analyzing the second image based on the retrieved grid alignment data.

In some additional embodiments, a method, or computer program product performing the method, includes aligning a grid with a first image, generating grid alignment data based on the alignment of the grid with the first image, storing the grid alignment data in memory, retrieving the grid alignment data responsive to an indication to analyze a second image, and analyzing the second image based on the retrieved grid alignment data, wherein the first image is generated by scanning a first probe array and the second image is generated by scanning a second probe array different from the first probe array.

The above embodiments, implementations, and aspects are not necessarily inclusive or exclusive of each other and may be combined in any manner that is non-conflicting and otherwise possible, whether they be presented in association with a same, or a different, aspect of the invention. The description of one embodiment, implementation, or aspect is not intended to be limiting with respect to other embodiments or implementations. Also, any one or more function, step, operation, or technique described elsewhere in this specification may, in alternative embodiments or implementations, be combined with any one or more function, step, operation, or technique described in the summary. Thus, the above embodiments, implementations, and aspects are illustrative rather than limiting.

BRIEF DESCRIPTION OF DRAWINGS

The above and further features will be more clearly appreciated from the following detailed description when taken in conjunction with the accompanying drawings. In the drawings, like reference numerals indicate like structures or method steps and the leftmost one or two digits of a reference numeral indicates the number of the figure in which the referenced element first appears (for example, the element 125 appears first in FIG. 1, the element 1010 first appears in FIG. 10). In functional block diagrams, rectangles generally indicate functional elements, parallelograms generally indicate data, and rectangles with a pair of double borders generally indicate predefined functional elements. In method flow charts, rectangles generally indicate method steps and diamond shapes generally indicate decision elements. All of these conventions, however, are intended to be typical or illustrative, rather than limiting.

DETAILED DESCRIPTION

Figure 1:
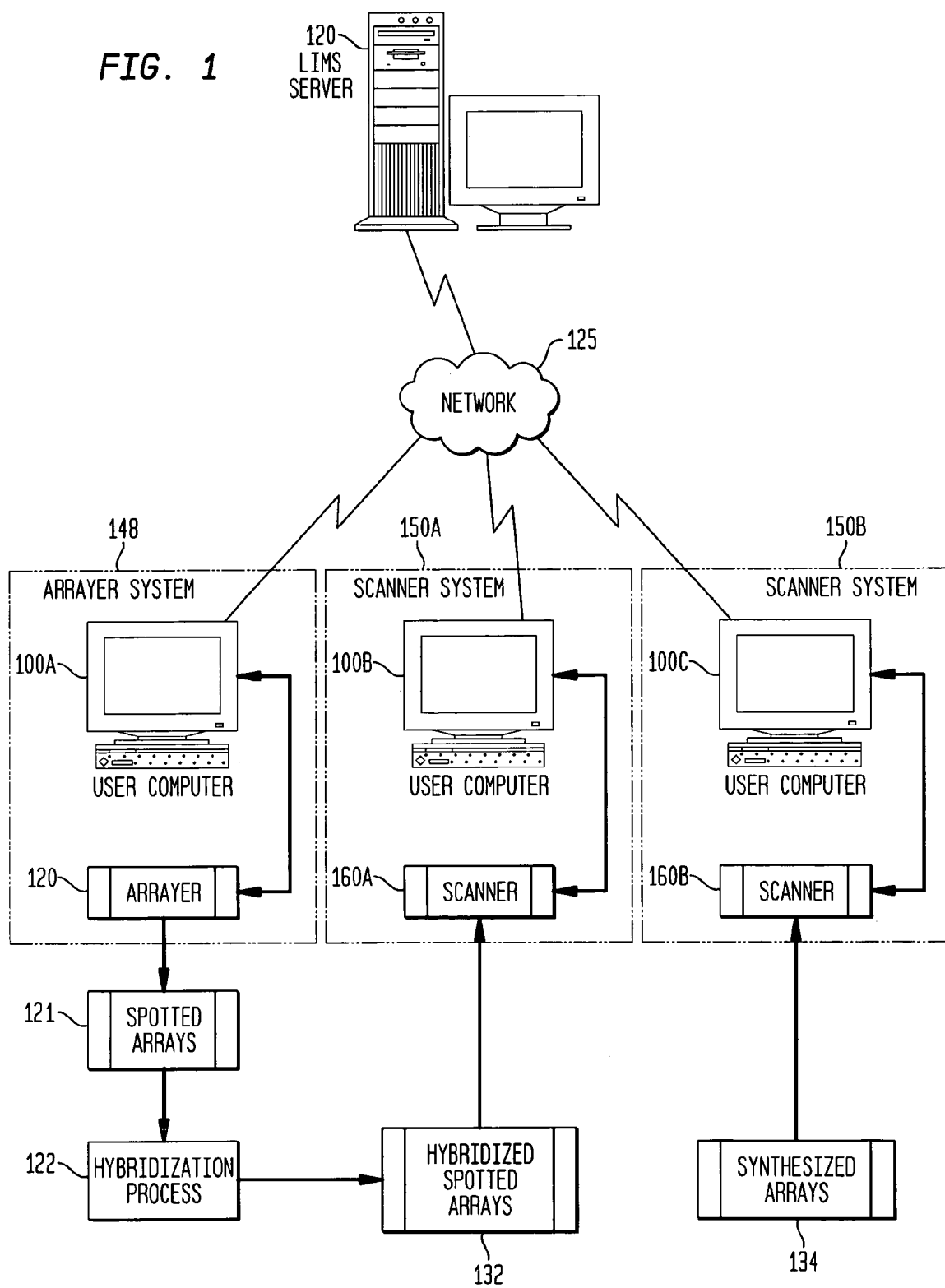
FIG. 1 is a simplified schematic diagram of one embodiment of networked systems for generating, sharing, and processing probe array data among computers on a network, including an arrayer system for generating spotted probe arrays and scanner systems for scanning spotted and synthesized probe arrays.

Systems, methods, and software products to acquire, process, analyze, and/or display data from experiments with synthesized and/or spotted arrays are described herein with respect to illustrative, non-limiting, implementations. Various other alternatives, modifications and equivalents are possible. For example, while certain systems, methods, and computer software products are described using exemplary embodiments with reference to spotted arrays analyzed using Affymetrix® scanners and/or Affymetrix software, the systems, methods, and products of the present invention are not so limited. For example, they generally may be applied with respect to many other probe arrays, including many types of parallel biological assays.

Probe Arrays

For example, certain systems, methods, and computer software products are described herein using exemplary implementations for acquiring, analyzing, and/or displaying data from arrays of biological materials produced by the Affymetrix® 417™ or 427™ Arrayer. Other illustrative implementations are referred to in relation to data from experiments with Affymetrix® GeneChip® arrays. However, these systems, methods, and products may be applied with respect to many other types of probe arrays and, more generally, with respect to numerous parallel biological assays produced in accordance with other conventional technologies and/or produced in accordance with techniques that may be developed in the future. For example, aspects of the systems, methods, and products described herein may, in some implementations, be applied to parallel assays of nucleic acids, PCR products generated from cDNA clones, proteins, antibodies, or many other biological materials. These materials may be disposed on slides (as typically used for spotted arrays), on substrates employed for GeneChip® arrays, or on beads, optical fibers, or other substrates, supports, or media (all or any of which may hereafter generally and collectively be referred to as substrates). Some implementations of synthesized arrays, their preparation, substrates, and the like are described in U.S. Pat. Nos. 5,744,305 and 5,445,934, which are hereby incorporated herein by reference in their entireties for all purposes. Moreover, with respect to some implementations in which the context so indicates or allows, the probes need not be immobilized in or on a substrate, and, if immobilized, need not be disposed in regular patterns or arrays. For convenience, the term probe array will generally be used broadly hereafter to refer to all of these types of arrays and parallel biological assays.

For convenience, an array made by depositing or positioning pre-synthesized or pre-selected probes on a substrate, or by depositing/positioning techniques that may be developed in the future, is hereafter referred to as a spotted array. Typically, but not necessarily, spotted arrays are commercially fabricated on microscope slides. These arrays often consist of liquid spots containing biological material of potentially varying compositions and concentrations. For instance, a spot in the array may include a few strands of short polymers, such as oligonucleotides in a water solution, or it may include a high concentration of long strands of polymers, such as complex proteins. The Affymetrix® 417™ and 427™ Arrayers, noted above, are devices that deposit densely packed arrays of biological material on a microscope slide in accordance with these techniques. Aspects of these, and other, spot arrayers are described in U.S. Pat. Nos. 6,121,048, 6,040,193 and 6,136,269, in PCT Applications Nos. PCT/US99/00730 (International Publication Number WO99/36760) and PCT/US 01/04285, in U.S. patent applications Ser. Nos. 09/122,216, 09/501,099, and 09/862,177, and in U.S. Provisional Patent Application Ser. No. 60/288,403, all of which are hereby incorporated by reference in their entireties for all purposes. Other techniques for depositing or positioning biological probes on a substrate, i.e., creating spotted arrays, also exist. For example, U.S. Pat. No. 6,040,193 to Winkler, et al. is directed to processes for dispensing drops of biological material. The '193 patent, and U.S. Pat. No. 5,885,837 to Winkler, also describe separating reactive regions of a substrate from each other by inert regions and spotting on the reactive regions. The '193 and '837 patents are hereby incorporated by reference in their entireties. Other techniques for producing spotted arrays are based on ejecting jets of biological material. Some implementations of the jetting technique use devices such as syringes or piezo electric pumps to propel the biological material.

Spotted arrays typically are used in conjunction with tagged biological samples such as cells, proteins, genes or EST's, other DNA sequences, or other biological elements. These samples, referred to herein as targets, typically are processed so that they are spatially associated with certain probes in the probe array. In one non-limiting implementation, for example, one or more chemically tagged biological samples, i.e., the targets, are distributed over the probe array. Some targets hybridize with at least partially complementary probes and remain at the probe locations, while non-hybridized targets are washed away. These hybridized targets, with their tags or labels, are thus spatially associated with the targets' complementary probes. The associated probe and target may sometimes be referred to as a probe-target pair. Detection of these pairs can serve a variety of purposes, such as to determine whether a target nucleic acid has a nucleotide sequence identical to or different from a specific reference sequence. See, for example, U.S. Pat. No. 5,837, 832 to Chee, et al. Other uses include gene expression monitoring and evaluation (see, e.g., U.S. Pat. No. 5,800,992 to Fodor, et al.; U.S. Pat. No. 6,040,138 to Lockhart, et al.; and International App. No. PCT/US98/15151, published as WO99/05323, to Balaban, et al.), genotyping (U.S. Pat. No. 5,856,092 to Dale, et al.), or other detection of nucleic acids. The '832, '992, '138, and '092 patents, and publication WO99/05323, are incorporated by reference herein in their entirety for all purposes.

To ensure proper interpretation of the term probe as used herein, it is noted that contradictory conventions exist in the relevant literature. The word probe is used in some contexts to refer not to the biological material that is deposited on a substrate, as described above, but to what has been referred to herein as the target. To avoid confusion, the term probe is used herein to refer to compounds such as those deposited on a substrate to create spotted arrays.

FIG. 1 is a simplified schematic diagram of illustrative systems for generating, sharing, and processing data derived from experiments using probe arrays (i.e., spotted arrays and/or synthesized arrays). More particularly, an illustrative arrayer system 148 and illustrative scanner systems 150A and 150B (collectively, scanner systems 150) are shown. In this example, data may be communicated among user computer 100A of system 148, user computers 100B and 100C of systems 150, and Laboratory Information Management (LIMS) server 120 over network 125. LIMS server 120 and associated software generally provides data capturing, tracking, and analysis functions from a centralized infrastructure. Aspects of a LIMS are described in U.S. Provisional Patent Application Nos. 60/220,587 and 60/273,231, both of which are hereby incorporated by reference herein for all purposes. LIMS server 120 and network 125 are optional, and the systems in other implementations may include a scanner for spotted arrays and not synthesized arrays, or vice versa. Also, rather than employing separate user computers 100A and 100B to operate and process data from an arrayer and scanner, respectively, as in the illustrated implementation, a single computer may be used for all of these purposes in other implementations. More generally, a large variety of computer and/or network architectures and designs may be employed, and it will be understood by those of ordinary skill in the relevant art that many components of typical computer network systems are not shown in FIG. 1 for sake of clarity.

Arrayer 120

The illustrative system of FIG. 1 includes an arrayer 120 for producing spotted arrays, such as represented by spotted arrays 121. For example, arrayer 120 may be the Affymetrix® 417™ or 427™ Arrayer (commercially available from Affymetrix, Inc. of Santa Clara, Calif.), elements of which are hereafter described to provide an example of how arrayer 120 may operate in a commercial embodiment. As noted above, however, numerous variations are possible in the technologies and structures that may be used to produce spotted arrays, and thus it will be understood that the following description of arrayer 120 is merely illustrative, and is non-limiting.

Arrayer 120 of the illustrated implementation deposits spots on substrates consisting of standard glass microscope slides. The slides are held on a flat platen or cartridge (not shown) that registers the slides relative to a printing head (not shown) that is lowered and raised to effect spotting. The spotting elements of the printing head may include, for example, various numbers of Affymetrix® Pin-and-Ring™ mechanisms, as described, e.g., in U.S. patent application Ser. No. 09/862,177, or U.S. Provisional Patent Application Ser. No. 60/288,403, incorporated by reference above. For example, the printing head in illustrative implementations may accommodate 1, 4, 8, 12, 32 or 48 pairs of pin and ring elements to deposit the spots of biological material onto the slide. Arrayer 120 thus may in some implementations be capable of rapidly depositing many spots of biological fluids, such as would be useful in preparing large numbers of DNA microarrays. The ring of the Pin-and-Ring™ mechanism in one implementation includes a circular ring section formed from a circular piece of metal. The ring is attached at the end of an arm section that extends from a cylinder. The pin in this example is a single, rod-like device having at one end a very narrow tip. During operation, the pin is inserted into and through the cylinder with the tip being capable of moving freely through the opening of the ring.

In some implementations, fluids to be spotted onto the microscope slides may be stored in and retrieved from well plates (also commonly referred to as microtiter plates) having, for example a standard number of 96 or 348 wells. The well plates loaded with fluids may, in some implementations, be inserted by a user into a carousel included in arrayer 120. Arrayer 120 may include a robotic system having an effector arm that, under computer control, may be instructed to retrieve a well plate from the carousel. Arrayer 120 may, in some implementations, be capable of automatically identifying well plates. For example, machine readable indicators, e.g., bar codes, may be attached to the well plates and a bar code reader may be attached to the robotic system for reading the bar codes. The robotic system pivots the retrieved well plate from the carousel to a well plate retainer on the platen. In other implementations, a user may manually place slides on the platen.

Arrayer 120 further includes a robotic system that may be instructed, under computer control, to position the printing head with respect to the well plate in the well plate retainer in order to obtain fluids from the well plate for spotting. For example, as described in U.S. patent application Ser. No. 09/862,177, referred to above, rings of the printing head may be lowered into the wells of the well plate while the pins of the printing head remain out of contact with the fluids. The ring section is then raised out of the fluids. Given the design of the rings, an amount of the fluid is retained within the rings by the surface tension of the fluid and the surface activity of the inner walls of the rings. After the rings are raised out of the sample solution, the fluid held in each ring forms a convex meniscus that protrudes from the bottom opening of the ring. The printing head, including the rings with fluids, can then be positioned at a location above a substrate (i.e., microscope slide in this example) onto which a fraction of the fluid in each ring is to be deposited. The fluid volume in the ring is sufficient to deposit or spot more than one fraction. In fact, several hundred to a thousand or more fractions can be deposited from a single fluid volume retained in a ring. The number of fractions will depend on the desired volume of each fraction, the dimensions of the pin and the viscosity of the fluid.

Once the pin and ring mechanism is position over the desired location on the substrate, the tip of the pin is then lowered into, through and out of the fluid retained in the ring. The surface tension of the fluid retains the fluid within the ring while the pin penetrates into and moves through and out of the fluid. A fraction of the fluid is retained on the tip of the pin forming a meniscus. The portion of the pin that passes through the ring has a diameter that typically is small compared to the diameter of the ring, enabling the pin to pierce the fluid without breaking the meniscus and causing the fluid to leave the ring.

The pin with the fluid on the tip is lowered toward the surface of the substrate until the meniscus of the fluid on the end of the pin makes initial contact with the surface of the substrate. During typical operation, the pin contacts the substrate without damaging force. The fluid then adheres via surface tension to the surface of the substrate, and as the pin is raised, the fluid is transferred to the surface of the substrate by surface tension and gravity. The pin is moved back through and above the fluid in the ring. The process of sample deposition can then be repeated by repositioning the pin and ring mechanism at another desired location above the surface of the substrate. Alternatively, the pin and ring can be positioned over another, different surface.

In this exemplary implementation, the printing head is positioned on an x-y gantry that is capable of moving the printing head across the length and width of the platen, and thus over numerous slides retained on the platen. For example, the printing head may move in a serpentine manner from slide to slide along a column of slides arranged on the platen, and then back along an adjacent column of slides on the platen. The movement of the printing head may be controlled in accordance with various techniques such as using sensors to count markers and arrive at a preprogrammed destination. The printing head may optionally be directed under computer control to wash and dry stations to clean the pins and rings between spotting applications.

User Computer 100A

As shown in FIG. 1 and noted above, arrayer 120 operates in the illustrated implementation under computer control, e.g., under the control of user computer 100A. Although computer 100A is shown in FIG. 1 for clarity as being directly coupled to arrayer 120, it may alternatively be coupled to arrayer 120 over a local-area, wide-area, or other network, including an intranet and/or the Internet.

Figure 2:
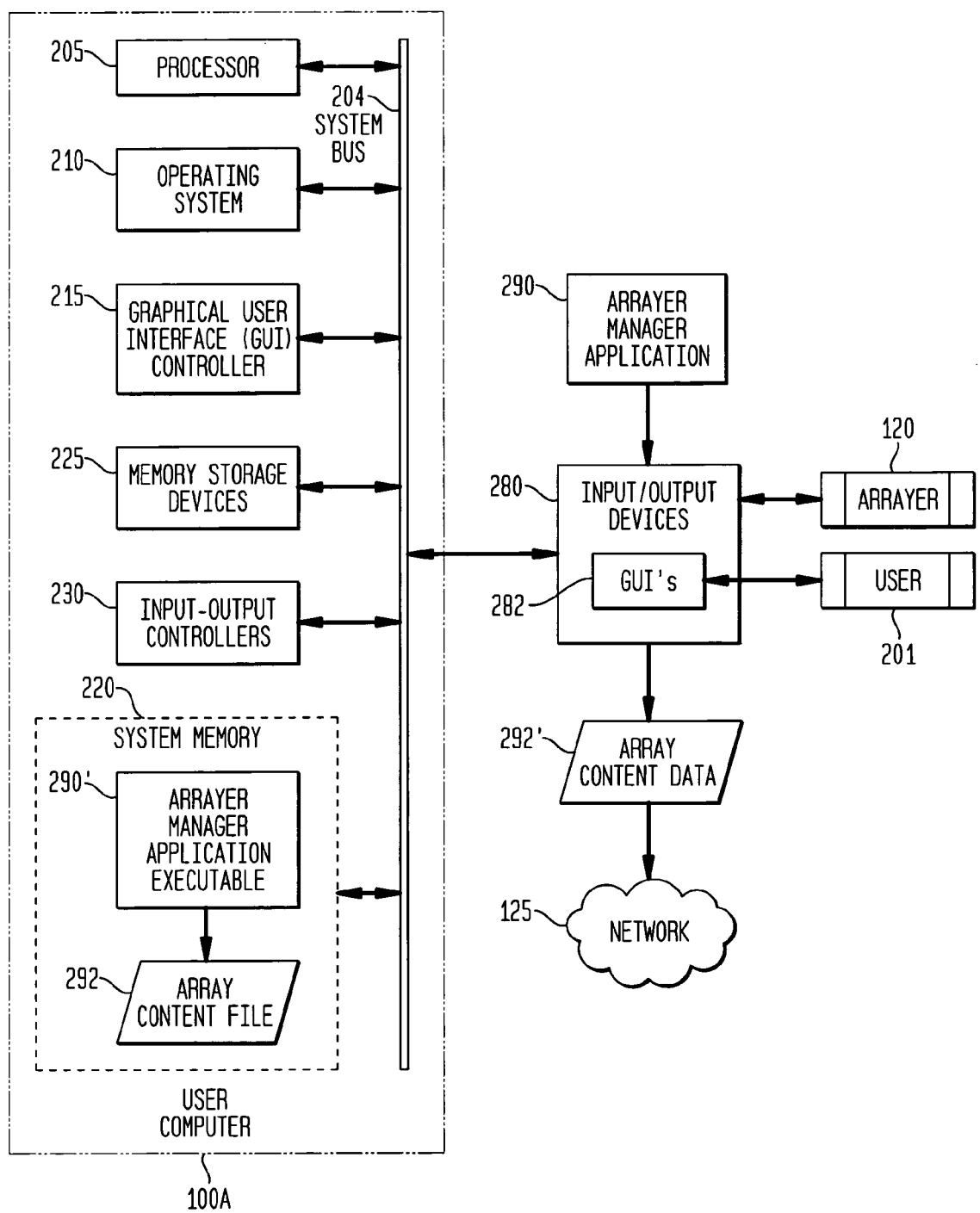
FIG. 2 is a functional block diagram of one embodiment of a user computer of the networked computers of FIG. 1 suitable for controlling the arrayer of FIG. 1 to produce spotted arrays.

FIG. 2 is a functional block diagram showing an illustrative implementation of computer 100A. Computer 100A may be a personal computer, a workstation, a server, or any other type of computing platform now available or that may be developed in the future. Typically, computer 100A includes known components such as processor (e.g., CPU) 205, operating system 210, system memory 220, memory storage devices 225, graphical user interface (GUI) controller 215, and input-output controllers 230, all of which typically communicate in accordance with known techniques such as via system bus 204. It will be understood by those skilled in the relevant art that there are many possible configurations of the components of computer 100A and that some components that may typically be included in computer 100A are not shown, such as cache memory, a data backup unit, and many other devices.

Input-output controllers 230 could include any of a variety of known devices for accepting and processing information from a user, whether a human or a machine, whether local or remote. Such devices include, for example, modem cards, network interface cards, sound cards, or other types of controllers for any of a variety of known input devices. Output controllers of input-output controllers 230 could include controllers for any of a variety of known display devices for presenting information to a user, whether a human or a machine, whether local or remote. If one of these display devices provides visual information, this information typically may be logically and/or physically organized as an array of picture elements, sometimes referred to as pixels. GUI controller 215 may comprise any of a variety of known or future software programs for providing graphical input and output interfaces between computer 100A and a user 201 e.g., an experimenter wishing to use arrayer 120 to generate spotted arrays), and for processing inputs from user 201 (hereafter sometimes referred to as user inputs or user selections).

Arrayer Manager Application 290

Arrayer manager application 290 of the illustrated implementation is a software application that controls functions of arrayer 120 and processes data supplied by user 201. As more particularly described with respect to certain implementations in U.S. Provisional Patent Application Ser. No. 60/288,403, incorporated by reference above, application 290, when executed in coordination with processor 205, operating system 210, and/or GUI controller 215, performs user interface functions, data processing operations, and data transfer and storage operations. For example, with respect to user interface functions, user 201 may employ one or more of GUI's 282 to specify and describe particular clones and their location in particular wells of particular well plates. Using another of GUI's 282, user 201 may specify how spots of the clones are to be arranged in arrays on one or more slides, as described in greater detail below with respect to fields 304 and 306 of array content file 292 shown in FIG. 3A. Yet another of GUI's 282 may be used to operate arrayer 120, e.g., to initiate the spotting of a number of slides without further user participation.

As will be evident to those skilled in the relevant art, application 290 may be loaded into system memory 220 and/or memory storage device 225 through an input device of devices 280. Alternatively, application 290 may be implemented as executable instructions stored in firmware. Executable code corresponding to application 290 is referred to as arrayer manager application executable 290' and is shown for convenience with respect to the illustrated implementation as stored in system memory 220. However, instructions and data including executable instructions of application 290, and data used or generated by it, may be located in or shifted among other memory devices, local or remote, as convenient for data storage, data retrieval, and/or execution.

Figure 3A:
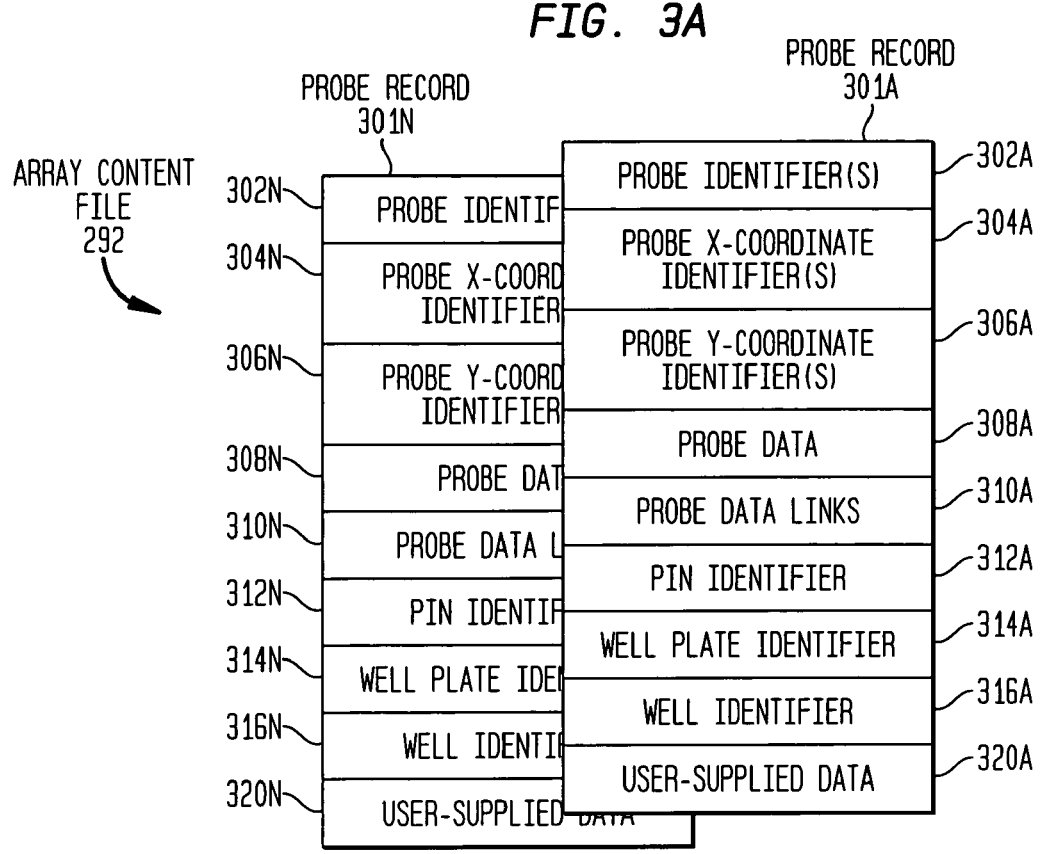
FIG. 3A is a graphical representation of data records in one embodiment of a data file suitable for storing data regarding spotted arrays produced in cooperation with the user computer of FIG. 2 and the arrayer of FIG. 1.
Figure 3B:
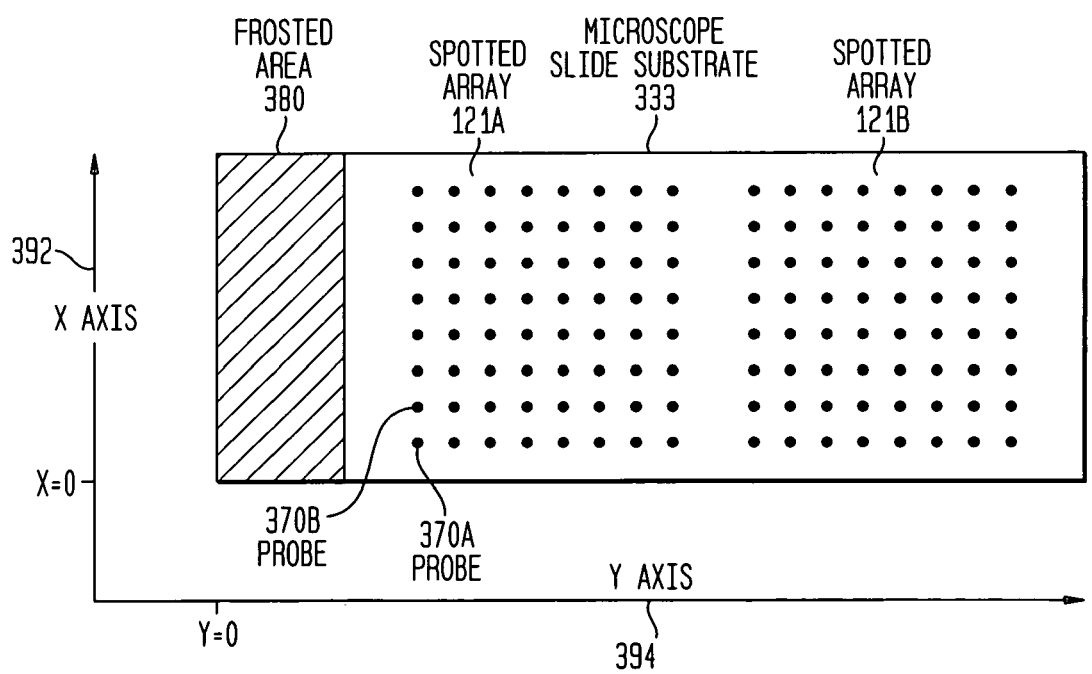
FIG. 3B is a graphical representation of a microscope slide including illustrative embodiments of spotted arrays produced in cooperation with the user computer of FIG. 2 and the arrayer of FIG. 1.

FIG. 3A is a graphical representation of illustrative data records in one implementation of a data file generated by arrayer manager application executable 290'. The data file in this illustration, referred to as array content file 292, consists of records 301, each one of which (i.e., records 301A through 301N for any number of N records) corresponds to one of N spots, i.e., probes, that have been deposited, or are planned to be deposited, on spotted arrays 121. For example, with reference to the graphical representation of spotted arrays 121 shown in FIG. 3B, two arrays 121A and 121B (collectively, arrays 121) have been printed on microscope slide substrate 333 by arrayer 120. Array 121A includes probe 370A. It is assumed for purposes of illustration that data relating to probe 370A is stored by executable 290' in probe record 301A. In this example, each of the records in file 292 includes the following illustrative fields: probe identifier(s) 302, probe x-coordinate identifier(s) 304, probe y-coordinate identifier(s) 306, probe data 308, probe data links 310, pin identifier 312, well plate identifier 316, and user-supplied data 320.

The field in record 301A labeled probe identifier(s) 302A thus, in this example, includes certain information related to the identification of probe 370A. For instance, field 302A may include a name for cDNA deposited by a pin of arrayer 120 in array 121A to produce probe 370A. In various implementations, field 302A may also, or in addition, include a nucleotide identifier and/or a gene symbol that identifies probe 370A. Also, field 302A may include a build or release number of a database so that the data source used to develop the probe can be identified. As yet another example of information that may be included in field 302A, a probe may be identified as either an original or as a replicate. For instance, for quality control or other reasons, probe 370B of array 121A may be the same probe as probe 370A, or a number of such replicate probes may be deposited. The designation of original or replicate number assists in comparing results from probes that are based on the same sample. As one of ordinary skill in the relevant art will readily appreciate, all or some of this identifying data may be stored as a single value in field 302A (such as, for example, concatenating name, nucleotide identifier, etc.), in separate fields (e.g., 302A', 302A", etc., not shown), in linked fields, and so on as may be convenient for data storage and/or processing. The other fields described below similarly are only representative of many possible storage and data retrieval architectures.

Field 308A, labeled probe data in this example, may include probe-related data such as the chromosome location of the gene or EST represented by the probe, the band location on the chromosome, a SNP or other type of marker that can identify the location on the chromosome, and so on. Field 310A, labeled probe data links in this example, similarly may include an accession number from GenBank, a UniGene cluster number, and/or another identifier that facilitates access to data related to probe 370A that is stored in a database. This database may, but need not, be external to computer 100A and accessed via network 125 and/or the Internet or other network. Systems for providing access to such information are described, for example, in U.S. Provisional Patent Application, Ser. No. 60/288,429, hereby incorporated herein by reference in its entirety. Field 312A of this example identifies the pin on the print head(s) that is used to deposit probe 370A onto the slide. This information may be useful in comparing probes deposited with the same pin to determine, for example, if the pin is defective. Fields 314A and 316A contain information that respectively identifies the well plate and particular well from which biological fluid was taken to create probe 370A. Field 320A may contain a variety of data supplied by user 201 such as the user's name, the data of the experiment, and so on. It will be understood that there are many other types of data relating to probe 370A that may be stored, and that numerous alternative arrangements may be implemented for storing them.

Fields 304A and 306A are used to identify the location of probe 370A on the slide in x and y coordinates, respectively. It will be understood that other coordinate systems (e.g., radial system) could be used, and that the definition of the orientation and zero points of the coordinate references of the present example are illustrative only. In one implementation of the present example, field 304A could include primary and secondary row coordinates, and field 306A could include primary and secondary column coordinates, that identify the position of probe 370A. For instance, arrays 121A and 121B could be viewed as arranged in a single primary column (disposed horizontally in FIG. 3B) in which array 121A occupies the first primary row and array 121B occupies the second primary row. Such an implementation may be said to involve relative, rather than absolute, locations because locations of probes are specified in relation to each other rather than in relation to a reference point on the substrate. It may be advantageous in some implementations to specify absolute, rather than relative, locations. In one such implementation, orthogonal x and y axes could be defined in relation to the sides of the microscope slide, such as x axis 392 and y axis 394 of the illustrated example, with the 0,0 reference coordinates defined with reference to a particular point on the slide. For instance, some slides are manufactured with a frosted area, such as area 380 of this example, so that a user may more easily label or write on the slide, or for other reasons. A particular point at a corner of the frosted area could readily be defined as the reference coordinate, or any of various other methods could be used to specify a reference coordinate on, or spatially related to, a point on the substrate.

Scanner 160A: Optics and Detectors

Any of a variety of conventional techniques, or ones to be developed in the future, may be used to generate probe-target pairs in probe arrays that may be detected using a scanner. As one illustrative example that will be familiar to those of ordinary skill in the relevant art, conventional fluidics stations, hybridization chambers, and/or various manual techniques (as, for example, generally and collectively represented by hybridization process 122 in FIG. 1) may be used to apply one or more labeled targets to spotted arrays on microscope slides. In a particular implementation, for instance, sample of a first target may be labeled with a first dye (an example of what may more generally be referred to hereafter as an emission label) that fluoresces at a particular characteristic frequency, or narrow band of frequencies, in response to an excitation source of a particular frequency. A second target may be labeled with a second dye that fluoresces at a different characteristic frequency. The excitation source for the second dye may, but need not, have a different excitation frequency than the source that excites the first dye, e.g., the excitation sources could be the same, or different, lasers. The target samples may be mixed and applied to the probes of spotted arrays on microscope slides, and conditions may be created conducive to hybridization reactions, all in accordance with known techniques. In accordance with other techniques, such as typically are applied with respect to Affymetrix® GeneChip® synthesized arrays, samples of one labeled target are applied to one array and samples of a second labeled target are applied to a second array having the same probes as the first array. Hybridization techniques are applied to both arrays. For example, synthesized arrays 134 of FIG. 1 may be illustratively assumed to be two GeneChip® synthesized arrays that have been subject to hybridization processes with respect to two different target samples, each labeled with different fluorescent dyes. See, e.g., U.S. Pat. No. 6,114,122, which is hereby incorporated by reference herein in its entirety.

Many scanner designs may be used to provide excitation signals to excite labels on targets or probes, and to detect the emission signals from the excited labels. In references herein to illustrative implementations, the term excitation beam may be used to refer to light beams generated by lasers to provide the excitation signal. However, excitation sources other than lasers may be used in alternative implementations. Thus, the term excitation beam is used broadly herein. The term emission beam also is used broadly herein. As noted, a variety of conventional scanners detect fluorescent or other emissions from labeled target molecules or other material associated with biological probes. Other conventional scanners detect transmitted, reflected, or scattered radiation from such targets. These processes are sometimes generally and collectively referred to hereafter for convenience simply as involving the detection of emission beams. The signals detected from the emission beams are generally referred to hereafter as emission signals and this term is intended to have a broad meaning commensurate with that intended herein for the term emission beams.

Various detection schemes are employed depending on the type of emissions and other factors. A typical scheme employs optical and other elements to provide an excitation beam, such as from a laser, and to selectively collect the emission beams. Also generally included are various light-detector systems employing photodiodes, charge-coupled devices, photomultiplier tubes, or similar devices to register the collected emission beams. For example, a scanning system for use with a fluorescently labeled target is described in U.S. Pat. No. 5,143,854, hereby incorporated by reference in its entirety for all purposes. Other scanners or scanning systems are described in U.S. Pat. Nos. 5,578,832, 5,631,734, 5,834,758, 5,936,324, 5,981,956, 6,025,601, 6,141,096, 6,185,030, 6,201,639, 6,218,803, and 6,252,236; in PCT Application PCT/US99/06097 (published as WO99/47964); in U.S. patent application Ser. No. 09/681,819; and in U.S. Provisional Patent Application Ser. No. 60/286,578, each of which also is hereby incorporated herein by reference in its entirety for all purposes.

Figure 4:
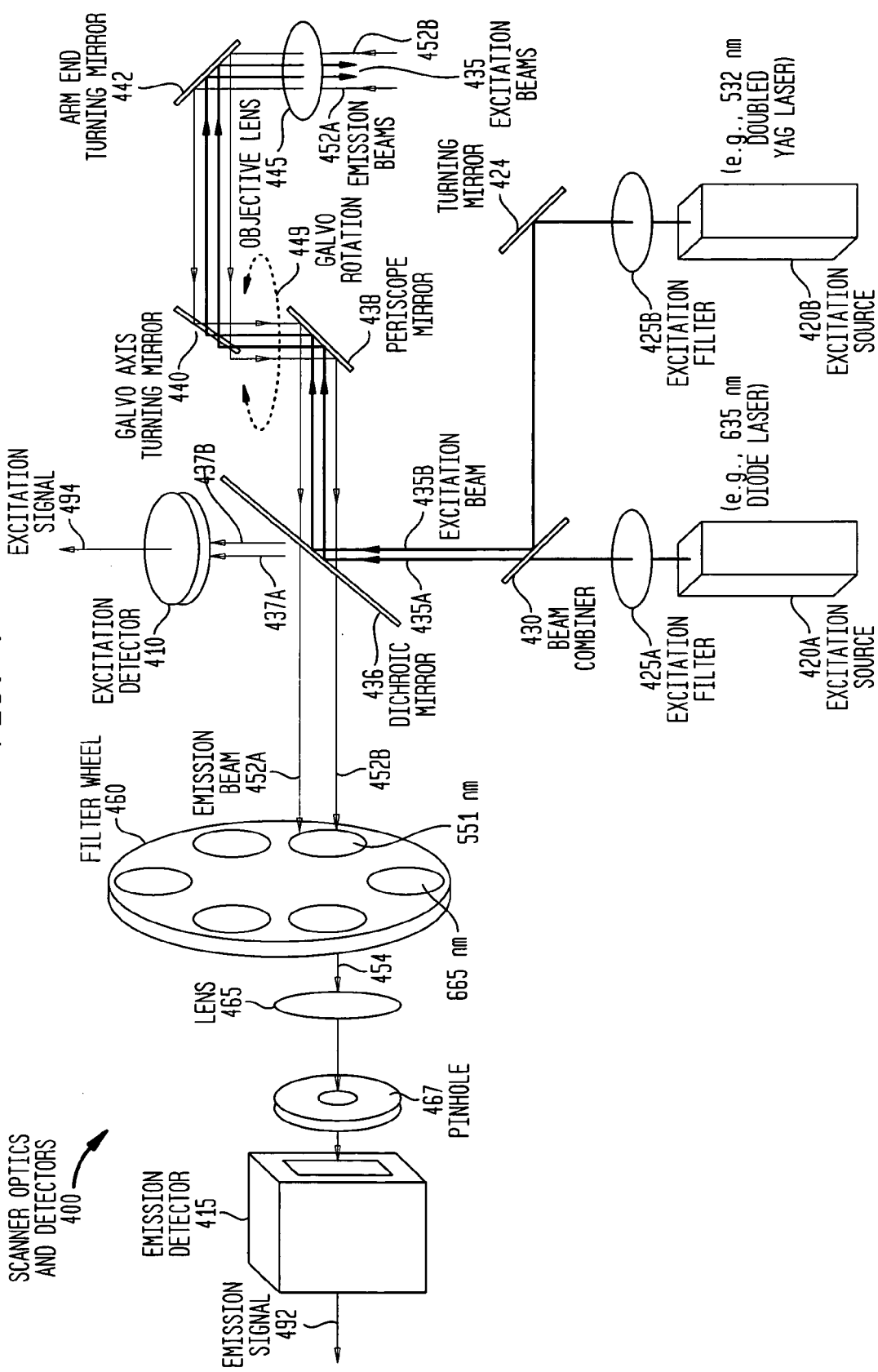
FIG. 4 is a simplified graphical representation of selected components of one embodiment of a scanner of FIG. 1 suitable for scanning arrays.

FIG. 4 is a simplified graphical representation of selected components of an illustrative type of scanner 160A suitable for scanning hybridized spotted arrays 132A and 132B disposed on slide 333 (i.e., in this example, spotted arrays 121A and 121B, respectively, after hybridization process 122). These illustrative components, which will be understood to be non-limiting and not exhaustive, are referred to collectively for convenience as scanner optics and detectors 400. Scanner optics and detectors 400 include excitation sources 420A and 420B (collectively referred to as excitation sources 420). Any number of one or more excitation sources 420 may be used in alternative embodiments. In the present example, sources 420 are lasers; in particular, source 420A is a diode laser producing red laser light having a wavelength of 635 nanometers and , source 420B is a doubled YAG laser producing green laser light having a wavelength of 532 nanometers. Further references herein to sources 420 generally will assume for illustrative purposes that they are lasers, but, as noted, other types of sources, e.g., x-ray sources, may be used in other implementations.

Sources 120A and 120B may alternate in generating their respective excitation beams 435A and 435B between successive scans, groups of successive scans, or between full scans of an array. Alternatively, both of sources 120 may be operational at the same time. For clarity, excitation beams 435A and 435B are shown as distinct from each other in FIG. 4. However, in practice, turning mirror 424 and/or other optical elements (not shown) typically are adjusted to provide that these beams follow the same path.

Scanner optics and detectors 400 also includes excitation filters 425A and 425B that optically filter beams from excitation sources 420A and 420B, respectively. The filtered excitation beams from sources 420A and 420B may be combined in accordance with any of a variety of known techniques. For example, one or more mirrors, such as turning mirror 424, may be used to direct filtered beam from source 420A through beam combiner 430. The filtered beam from source 420B is directed at an angle incident upon beam combiner 430 such that the beams combine in accordance with optical properties techniques well known to those of ordinary skill in the relevant art. Most of combined excitation beams 435 are reflected by dichroic mirror 436 and thence directed to periscope mirror 438 of the illustrative example. However, dichroic mirror 436 has characteristics selected so that portions of beams 435A and 435B, referred to respectively as partial excitation beams 437A and 437B and collectively as beams 437, pass through it so that they may be detected by excitation detector 410, thereby producing excitation signal 494.

Figure 5A:
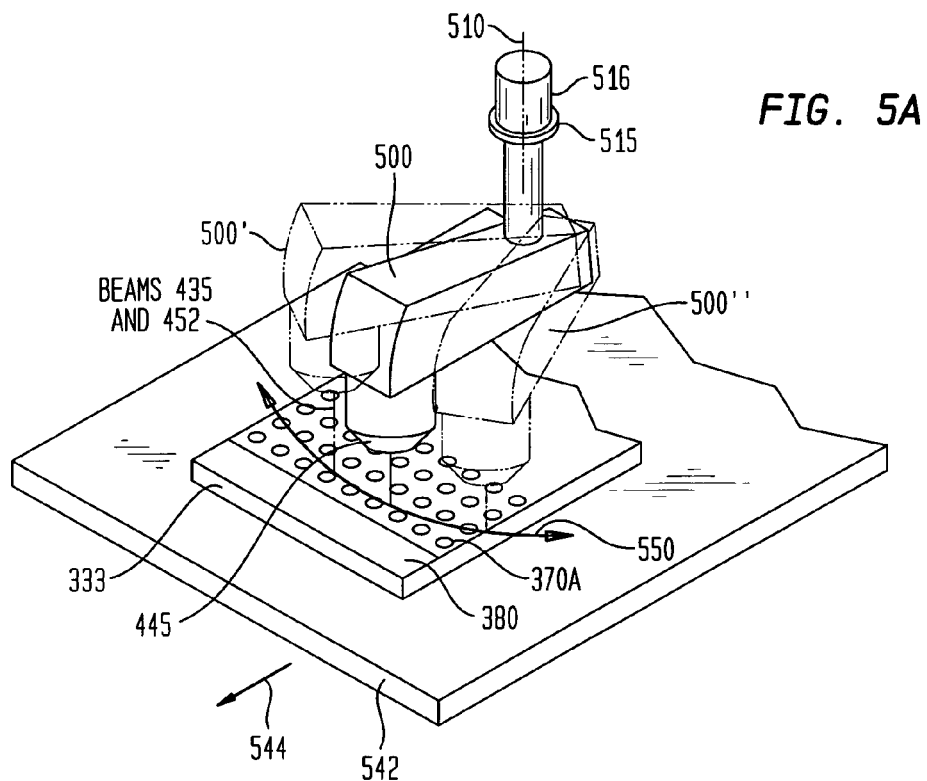
FIG. 5A is a perspective view of a simplified exemplary configuration of a scanning arm portion of the scanner of FIG. 4.
Figure 5B:
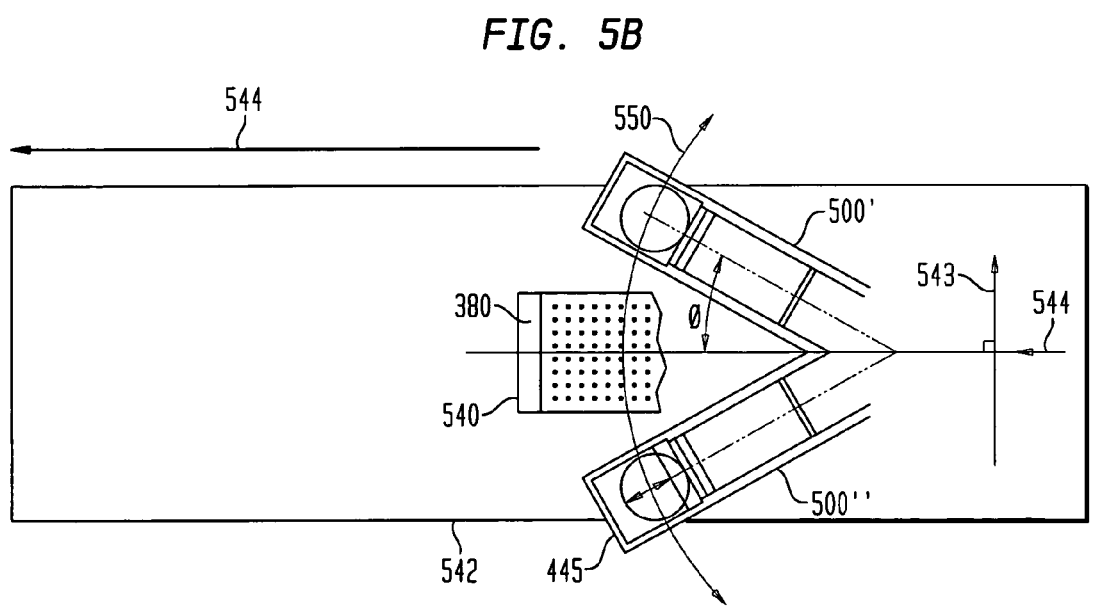
FIG. 5B is a top planar view of the scanning arm of FIG. 5A as it scans biological features on one embodiment of a spotted array being moved by a translation stage under the arm's arcuate path.

In the illustrated example, excitation beams 435 are directed via periscope mirror 438 and arm end turning mirror 442 to an objective lens 445. As shown in FIGS. 5A and 5B, lens 445 in the illustrated implementation is a small, light-weight lens located on the end of an arm that is driven by a galvanometer around an axis perpendicular to the plane represented by galvo rotation 449 shown in FIG. 4. Objective lens 445 thus, in the present example, moves in arcs over hybridized spotted arrays 132 disposed on slide 333. Flourophores in hybridized probe-target pairs of arrays 132 that have been excited by beams 435 emit emission beams 452 (beam 452A in response to excitation beam 435A, and beam 452B in response to excitation beam 435B) at characteristic wavelengths in accordance with well known principles. Emission beams 452 in the illustrated example follows the reverse path as described with respect to excitation beams 435 until reaching dichroic mirror 436. In accordance with well known techniques and principles, the characteristics of mirror 436 are selected so that beams 452 (or portions of them) pass through the mirror rather than being reflected.

In the illustrated implementation, filter wheel 460 is provided to filter out spectral components of emission beams 452 that are outside of the emission band of the fluorophore, thereby providing filtered beams 454. The emission band is determined by the characteristic emission frequencies of those fluorophores that are responsive to the frequencies of excitation beams 435. In accordance with techniques well known to those of ordinary skill in the relevant arts, including that of confocal microscopy, filtered beams 454 may be focused by various optical elements such as lens 465 and also passed through illustrative pinhole 467 or other element to limit the depth of field, and thence impinges upon emission detector 415.

Emission detector 415 may be a silicon detector for providing an electrical signal representative of detected light, or it may be a photodiode, a charge-coupled device, a photomultiplier tube, or any other detection device that is now available or that may be developed in the future for providing a signal indicative of detected light. For convenience of illustration, detector 415 will hereafter be assumed to be a photomultiplier tube (PMT). Detector 415 thus generates emission signal 492 that represents numbers of photons detected from filtered emission beam 454.

FIG. 5A is a perspective view of a simplified representation of the scanning arm portion of scanner optics and detectors 400. Arm 500 moves in arcs around axis 510, which is perpendicular to the plane of galvo rotation 449. A position transducer 515 is associated with galvanometer 515 that, in the illustrated implementation, moves arm 500 in bi-directional arcs. Transducer 515, in accordance with any of a variety of known techniques, provides an electrical signal indicative of the radial position of arm 500. Certain non-limiting implementations of position transducers for galvanometer-driven scanners are described in U.S. Pat. No. 6,218,803, which is hereby incorporated by reference in its entirety for all purposes. The signal from transducer 515 is provided in the illustrated implementation to user computer 100B so that clock pulses may be provided for digital sampling of emission signal 492 when arm 500 is in certain positions along its scanning arc.

Arm 500 is shown in alternative positions 500' and 500" as it moves back and forth in scanning arcs about axis 510. Excitation beams 435 pass through objective lens 445 on the end of arm 500 and excite fluorophore labels on targets hybridized to certain of probes 370 in arrays 132 disposed on slide 333, as described above. The arcuate path of excitation beams 435 is schematically shown for illustrative purposes as path 550. Emission beams 452 pass up through objective lens 445 as noted above. Slide 333 of this example is disposed on translation stage 542 that is moved in what is referred to herein as the y direction 544 so that arcuate path 550 repeatedly crosses the plane of arrays 132.

FIG. 5B is a top planar view of arm 500 with objective lens 445 scanning arrays 132 as translation stage 542 is moved under path 550. As shown in FIG. 5B, arcuate path 550 of this example is such that arm 500 has a radial displacement of θ in each direction from an axis parallel to direction 544. What is referred to herein as the x direction, perpendicular to y-direction 544, is shown in FIG. 5B as direction 543. Further details of confocal, galvanometer-driven, arcuate, laser scanning instruments suitable for detecting fluorescent emissions are provided in PCT Application PCT/US99/06097 (published as WO99/47964) and in U.S. Pat. Nos. 6,185,030 and 6,201,639, all of which have been incorporated by reference above. It will be understood that although a galvanometer-driven, arcuate, scanner is described in this illustrative implementation, many other designs are possible, such as the voice-coil-driven scanner described in U.S. patent application Ser. No. 09/383,986, hereby incorporated herein by reference in its entirety for all purposes.

Figure 6A:
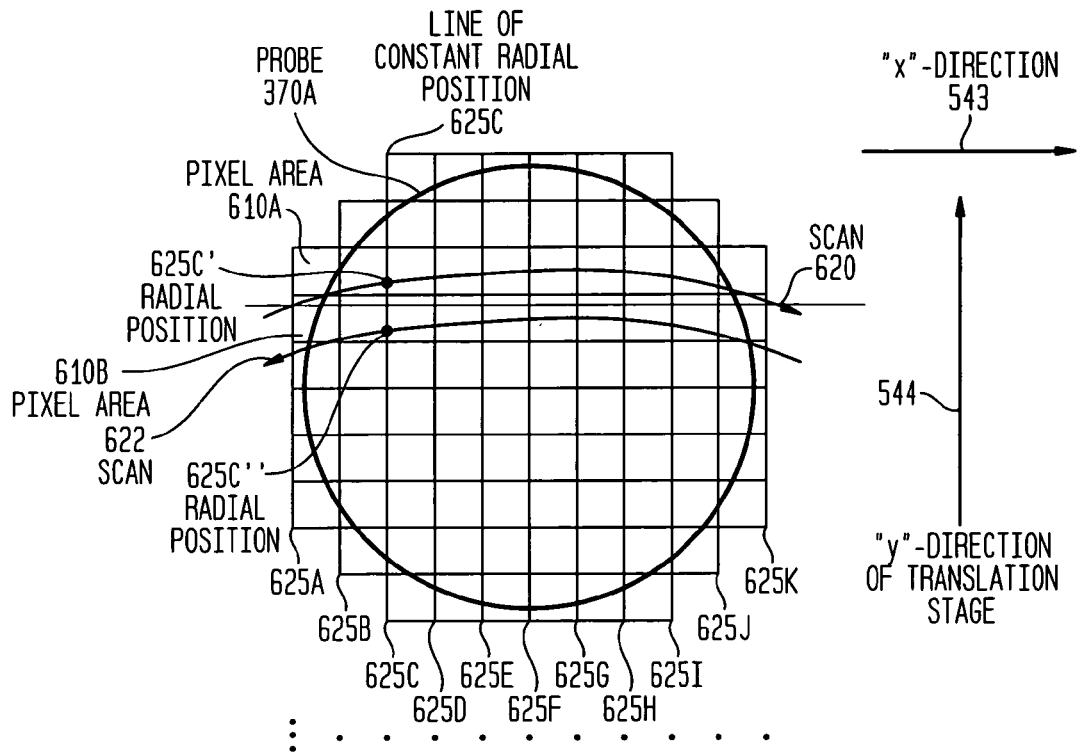
FIG. 6A is a graphical representation of one embodiment of a probe feature showing bi-directional scanning lines such as may be implemented using the scanning arm of FIGS. 5A and 5B.

FIG. 6A is a simplified graphical representation of illustrative probe 370A as it is scanned by scanner 160A. It is assumed for illustrative purposes that probe 370A has hybridized with a fluorescently labeled target. Although FIG. 6A shows probe 370A in idealized form, i.e. a perfect circle, it will be understood that many shapes, including irregular shapes, are possible.

In the manner described above, objective lens 445 scans over probe 370A (and other probes of arrays 132) in bi-directional arcs. An illustrative scan 620 is shown in FIG. 6A, which is not necessarily drawn to scale; e.g., the ratio of the radius of the arc of scan 620 to the radius of probe 370A is illustrative only. As also noted, probe 370A moves under objective lens 445 carried by translation stage 542 in y-direction 544. In particular, in the illustrated implementation, arm 500 scans in an arc in one direction, shown as left-to-right scan 620 in FIG. 6A. Translation stage 542 is then moved incrementally by a stepping motor (not shown) in y-direction 544 and arm 500 then scans back in the opposite direction, shown as right-to-left arcuate scan 622. Translation stage 542 is again moved in direction 544, and so on in scan-step-scan-step sequences. The distance between scans 620 and 622 thus corresponds to the distance that translation stage 542 is moved in each increment, although it will be understood that the distance shown in FIG. 6A is not necessarily to scale and is illustrative only. It will be understood that any other combination of scanning and stepping is possible in alternative implementations, and that scanning and moving of translation stage 542 may occur at the same or at overlapping times in some implementations. Translation stage 542 need not be stepped in some implementations, but may, for example, be moved continuously.

Figure 6B:
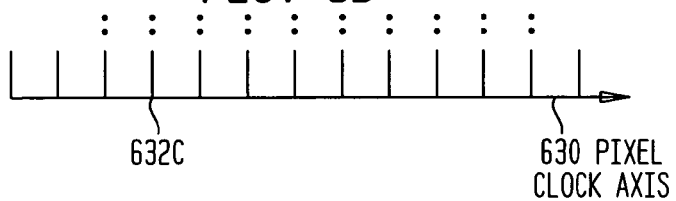
FIG. 6B is an illustrative plot of pixel clock pulses aligned with the scanned probe feature of FIG. 6A to show illustrative radial position sampling points.

FIG. 6B is a plot having a pixel clock axis 630 showing when clock pulses 632 occur. Clock pulses 632 may be generated by a pixel clock of scanner 160A (e.g., complex programmable logic device 830, described below) or, alternatively, they may be generated by software executing in computer 100B (e.g., executable 790', described below). Axis 630 in the illustrated implementation is a spatial axis; that is, each of clock pulses 632 occurs in reference to the radial location of arm 500 during each scan, as described in greater detail below. Thus, with reference to the position of translation stage 542 indicated by scan 620, a clock pulse 632A occurs prior to arm 500 passing over probe 370A from the left as shown in FIGS. 6A and 6B. (For sake of clarity of illustration only, vertical dotted lines are provided between FIGS. 6A and 6B, and between FIGS. 6B and 6C, to illustrate the alignment of these figures.) As another example, clock pulse 632C occurs with respect to scan 620 when arm 500 has just passed over portions of probe 370A indicated by pixel areas 610A and 610B. These areas are referred to as pixel areas because a digital value is assigned to each such area in the illustrated implementation based on the strength of a processed emission signal associated with that area. In accordance with known techniques, clock pulses 632 enable the digital sampling of the processed emission signal.

As noted, clock pulses 632 are spatially rather than temporally determined in the illustrated implementation. Moreover, in some aspects of the illustrated implementation, galvanometer 516 is driven by a control signal provided by user computer 100B such that the velocity of arm 500 in x-direction 444 is constant in time during those times when arm 500 is over probe 370A (and, typically, over other of probes 370 of arrays 132 as they are scanned). That is, dx/dt is a constant (and thus the angular velocity varies) over the probe-scanning portions of each arc and, in particular, it is a constant during the times when clock pulses are generated to enable digital sampling. As is evident, dx/dt must be reduced to zero between each successive scan, but this deceleration and reversal of direction takes place after arm 500 has passed over probe 370A (or, more generally, array 132A or 132B). The design and implementation of a galvanometer control signal to provide constant dx/dt are readily accomplished by those of ordinary skill in the relevant art.

Thus, the approximate sampling rate may readily be calculated based on the desired scanning speed (dx/dt) and desired pixel resolution. To provide an illustrative example, a spot deposited by an Affymetrix® 417™ or 427™ Arrayer typically has a diameter of approximately 150 to 200 microns. Spotted arrays made using these instruments typically may be deposited over a surface having a width of about 22 millimeters on a microscope slide that is 25 millimeters wide. In order to achieve pixel resolution of about 10 microns, a sampling rate of about 160 kHz is sufficient for scanning speeds typical for scanners used with respect to these probe arrays, such as the Affymetrix® 428™ scanner. Other sampling rates, readily determined by those of ordinary skill, may be used in other applications in which, for example, different scanning speeds are used and/or different pixel resolutions are desired. The desired pixel resolution typically is a function of the size of the probe features, the possibility of variation in detected fluorescence within a probe feature, and other factors.

Figure 6C:
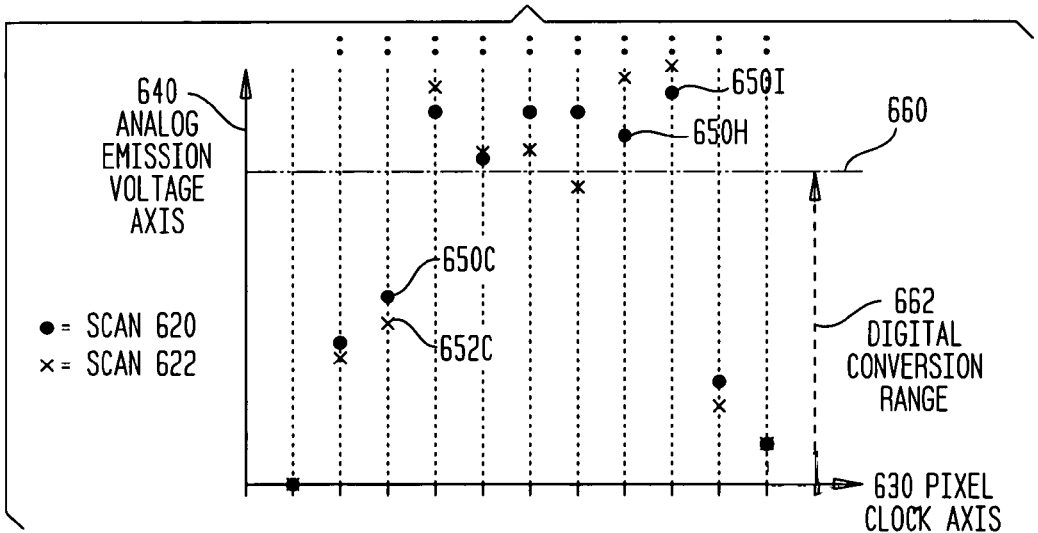
FIG. 6C is an illustrative plot of sampled analog emission voltages aligned with the pixel clock pulses of FIG. 6B.

FIG. 6C shows digital values representative of emission signal 492 as sampled at (and/or collected for an adjoining period before) points on scans 620 and 622 represented by constant radial position lines 625A–K (collectively referred to as radial position lines 625). The voltages sampled during scan 620 are shown as dots, while the voltages sampled during scan 622 are shown as x's. The determination of when to initiate pixel clock signals may be made using position transducer 515, as described in greater detail in U.S. Provisional Patent Application Ser. No. 60/286,578, incorporated by reference above. Thus, for example, voltage 650C of FIG. 6C is representative of emission signal 492 based on sampling enabled by a pixel clock pulse at point 632C on axis 630 that is triggered when arm 500 is at radial position 625C during scan 620. After translation stage 542 has been incremented, voltage 652C is sampled during scan 622 at the same radial position, shown as radial position 625C".

User Computer 100B

Figure 7:
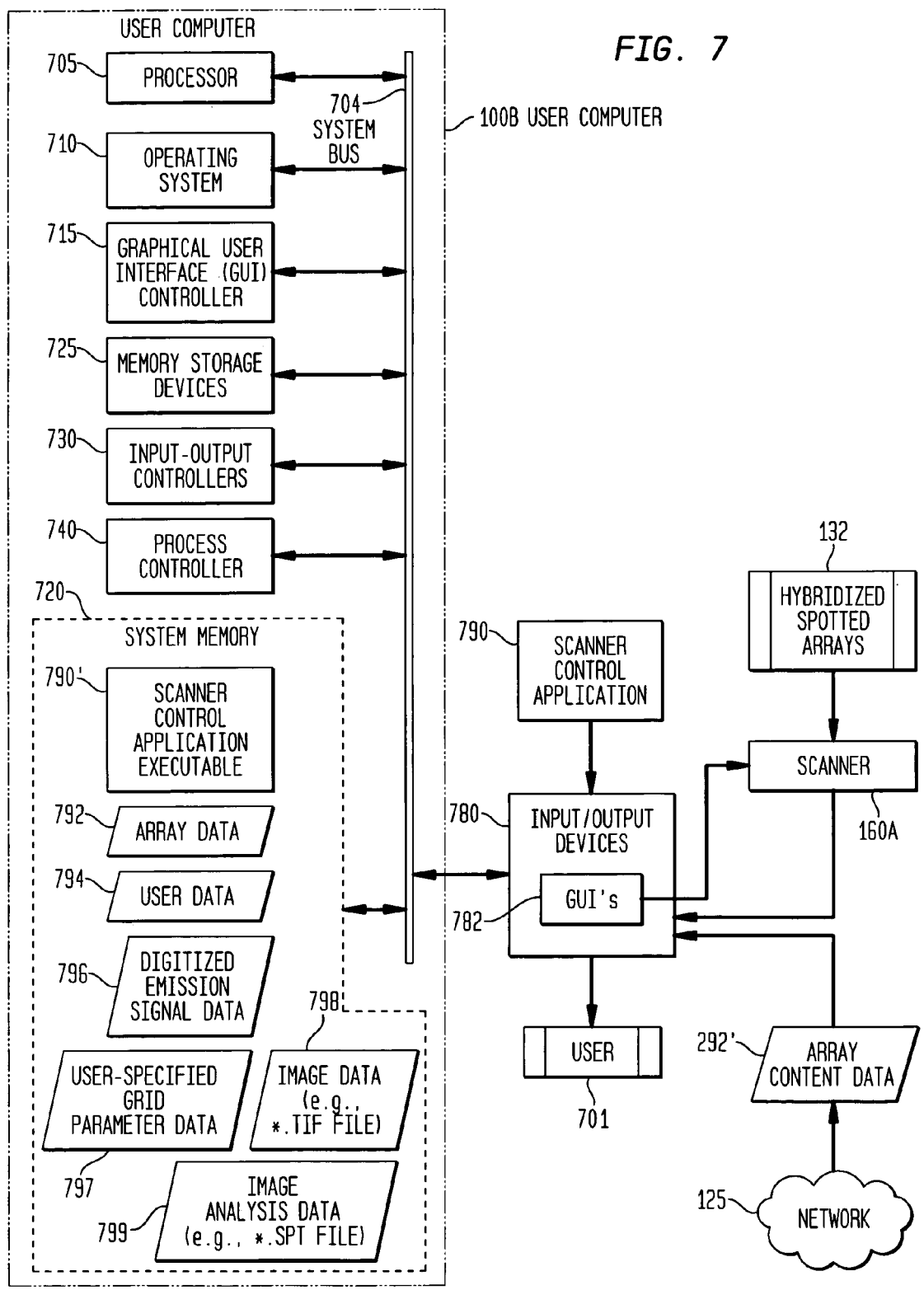
FIG. 7 is a functional block diagram of one embodiment of a scanner system of FIG. 1.

As shown in FIG. 1 and noted above, scanner 160B operates in the illustrated implementation under computer control, e.g., under the control of user computer 100B, as shown in greater detail in FIG. 7. Although computer 100B is shown in FIGS. 1 and 7 for clarity as being directly coupled to scanner 160A, it may alternatively be coupled to scanner 160A over a local-area, wide-area, or other network, including an intranet and/or the Internet. Computer 100B may be a personal computer, a workstation, a server, or any other type of computing platform now available or that may be developed in the future. Typically, computer 100B includes known components such as processor (e.g., CPU) 705, operating system 710, system memory 720, memory storage devices 725, GUI controller 715, and input-output controllers 730, all of which typically communicate in accordance with known techniques such as via system bus 704. It will be understood by those skilled in the relevant art that there are many possible configurations of the components of computer 100B and that some components that may typically be included in computer 100B are not shown, such as cache memory, a data backup unit, and many other devices.

Input-output controllers 730 could include any of a variety of known devices for accepting and processing information from a user, whether a human or a machine, whether local or remote. Such devices include, for example, modem cards, network interface cards, sound cards, or other types of controllers for any of a variety of known input devices. Output controllers of input-output controllers 730 could include controllers for any of a variety of known display devices for presenting information to a user, whether a human or a machine, whether local or remote. If one of these display devices provides visual information, this information typically may be logically and/or physically organized as an array of picture elements, sometimes referred to as pixels. Graphical user interface (GUI) controller 715 may comprise any of a variety of known or future software programs for providing graphical input and output interfaces between computer 100B and a user 701 (e.g., an experimenter wishing to use scanner 160A to acquire and analyze information from spotted arrays), and for processing inputs from user 701 (hereafter sometimes referred to as user inputs or user selections). To avoid confusion, references hereafter to a GUI generally are directed to one or more graphical user interfaces displayed on a display device of devices 780 to user 701, such as GUI 782A of FIGS. 8 and 9, described below. To be distinguished are references to a GUI controller, such as GUI controller 715, that operates to display the GUI's to user 701 and to process input information provided by user 701 through the GUI's. As is well known in the relevant art, a user may provide input information using a GUI by selecting, pointing, typing, speaking, and/or otherwise operating, or providing information into, one or more input devices of devices 780 in a known manner.

Computer 100B may optionally include process controller 740 that may, for example, be any of a variety of PC-based digital signal processing (DSP) controller boards, such as the M44 DSP Board made by Innovative Integration of Simi Valley, Calif. More generally, controller 740 may be implemented in software, hardware or firmware, or any combination thereof.

Scanner Control and Analysis Application 790

Scanner control application 790 of the illustrated implementation is a software application that controls functions of scanner 160A. In addition, when executed in coordination with processor 705, operating system 710, GUI controller 715, and/or process controller 740, application 790 performs user interface functions, data and image processing operations, and data transfer and storage operations related to data provided by or to scanner 160A and/or user 701, as described in greater detail below. Affymetrix® Jaguar™ software, available from Affymetrix, Inc., is a commercial product that, in some implementations, includes various aspects of application 790.

Figure 8:
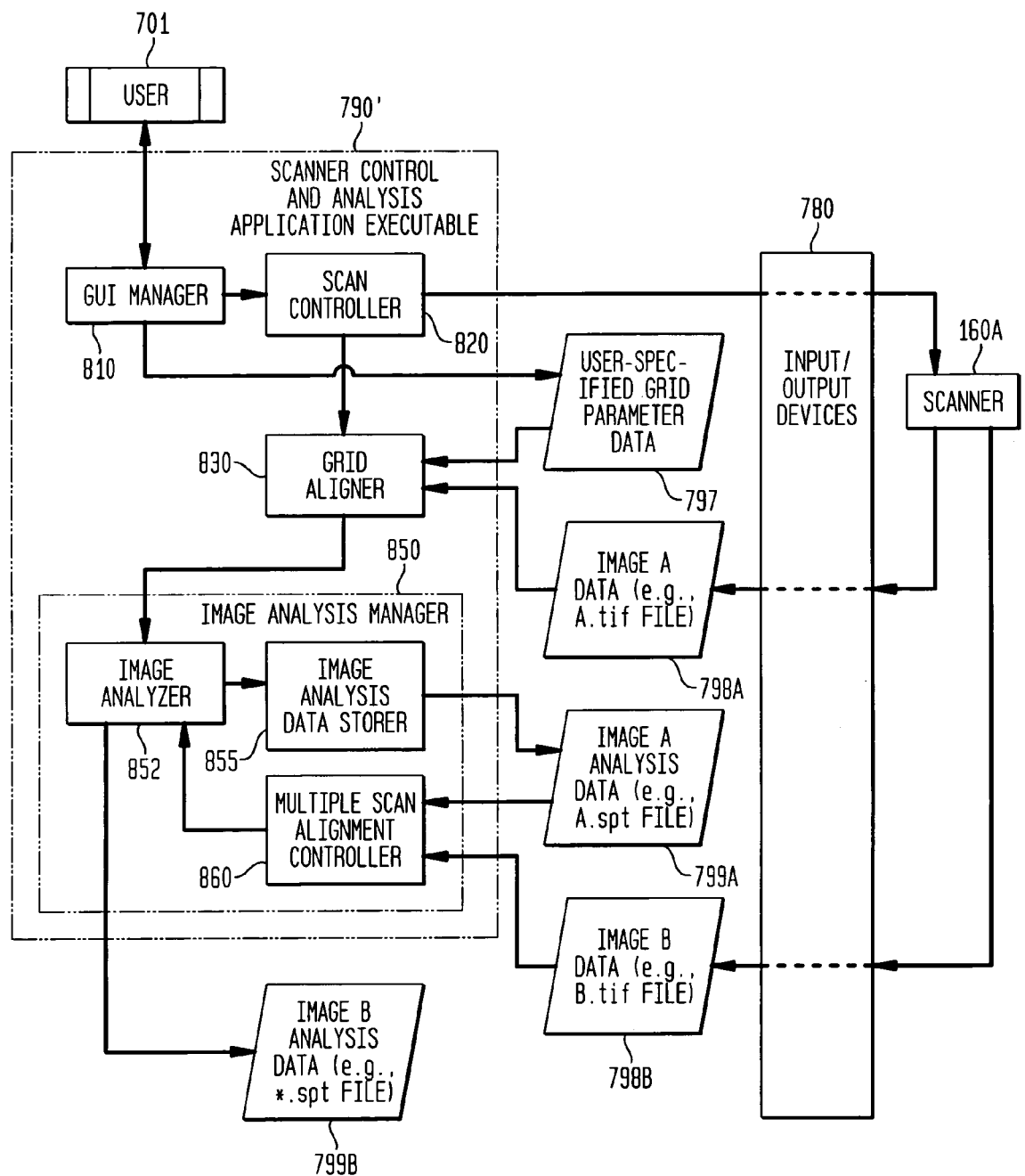
FIG. 8 is functional block diagram of one embodiment of a scanner control and analysis application (i.e., computer program product)

As more particularly shown in FIG. 8, scanner control application 790 in the illustrated implementation includes a GUI manager 810 that receives one or more user-selected grid aligning parameters. Also included in application 790 is grid aligner 830 that aligns a grid with a first image. Another element of application 790 in this implementation is image analysis manager 850 that includes image analyzer 852, image analysis data storer 855, and multiple scan alignment controller 860. Image analyzer 852 generates grid alignment data based on the alignment of the grid with the first image. Image analysis data storer 855 stores the grid alignment data in memory, such as in illustrative image A analysis data file 799A that, as shown in FIG. 7, may be stored in system memory 720 of computer 100B. Multiple scan alignment controller 860 in this implementation retrieves the grid alignment data (e.g., from file 799A) responsive to an indication to align a second image. Image analyzer 852 analyzes the second image based on the retrieved grid alignment data. These operations are now further described with reference to the GUI's of FIGS. 9 and 10 and the illustrative images of FIGS. 11A and 11B. The relations of these operations to method steps of the illustrative flow chart of FIG. 12 are parenthetically indicated.

Figure 9:
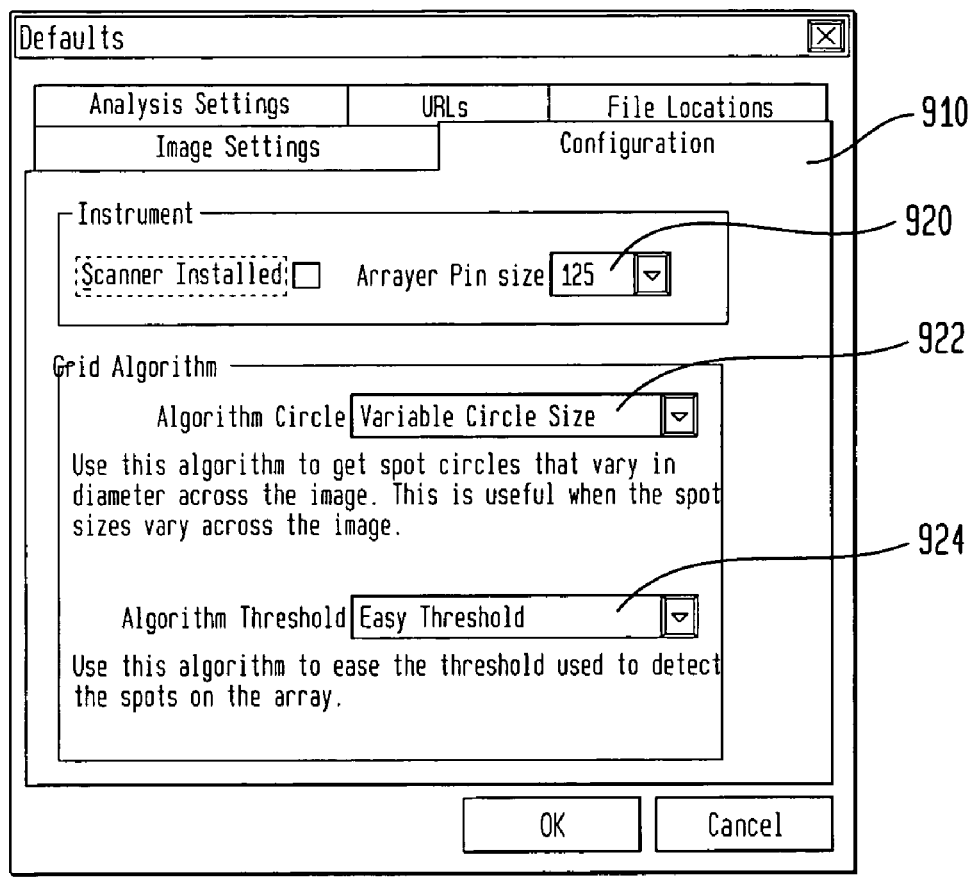
FIG. 9 is an illustrative implementation of a graphical user interface employed in cooperation with the application of FIG. 8 to receive user-specified grid parameter data.

In the present example, it is illustratively assumed that GUI manager 810 provides GUI 782A of FIG. 9 to user 701, typically in response to a user selection. User 701 employs GUI 782A to select illustrative grid aligning parameters (see corresponding step 1210 of FIG. 12). For example, as indicated by graphical elements 922 and 924, user 701 may select whether grid alignment is to be done using a fixed algorithm shape with an easy threshold, a fixed algorithm shape with tight threshold, a variable algorithm shape with easy threshold, or a variable algorithm shape with tight threshold. In the illustrated implementation, a selection of variable circle size, for instance, indicates that grid aligner 830 should use circles of varying diameter independently to identify pixels to represent each probe feature in the array image.

Figure 11A:
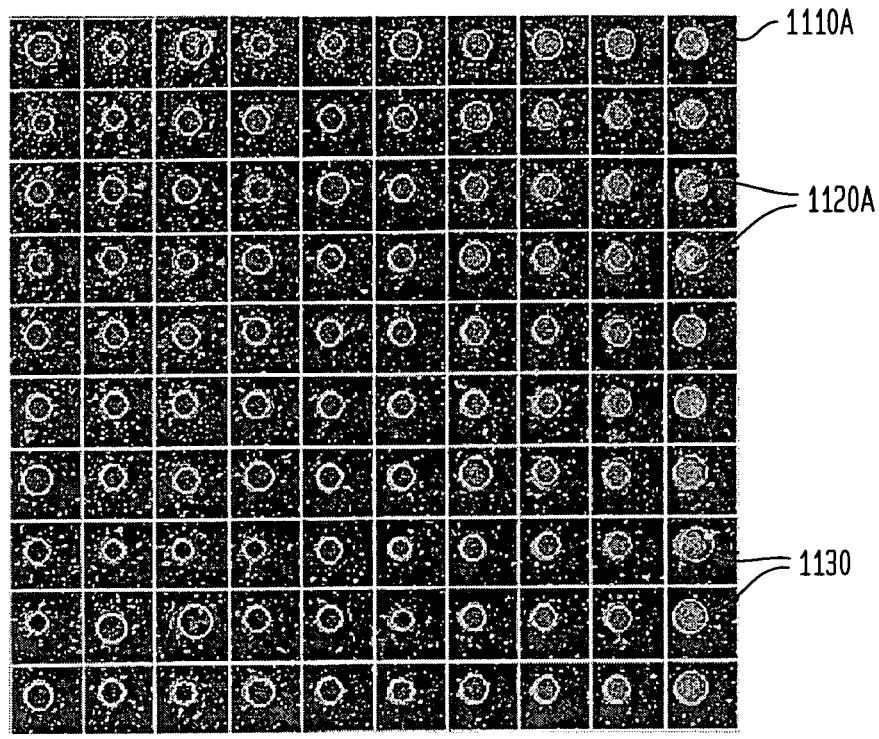
FIGS. 11A and 11B are graphical representations of scanned images showing the application of a grid and of user-specified grid parameter data.
Figure 11B:
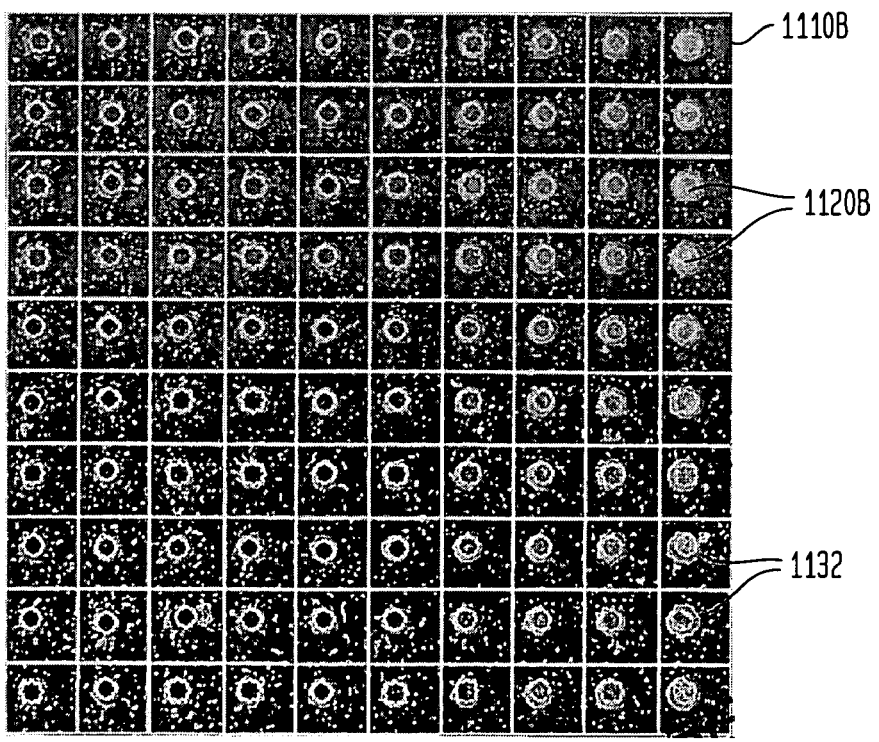
Figure 12:
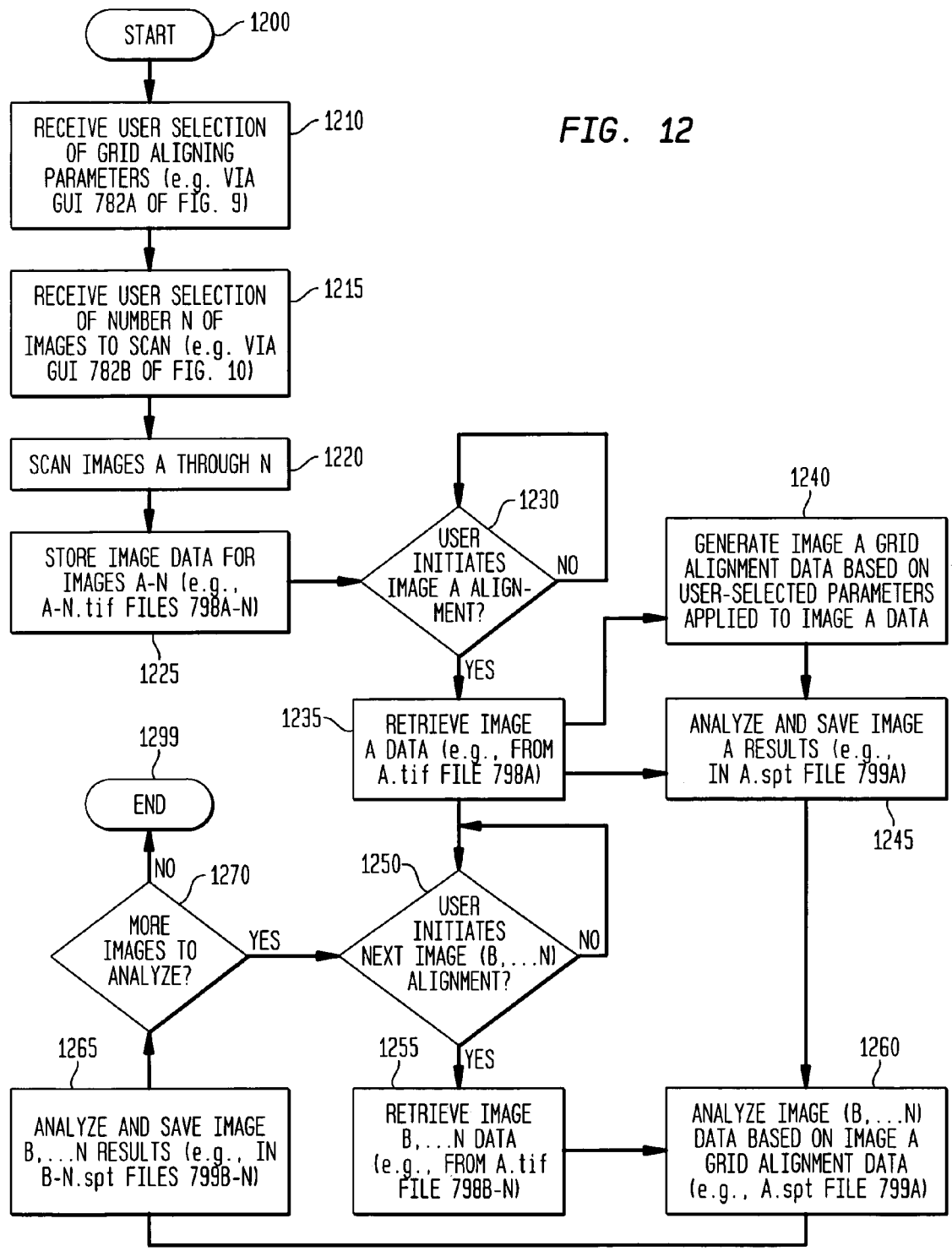
FIG. 12 is a flow diagram showing steps implemented by illustrative embodiments of the application of FIG. 8.

For example, FIG. 11A shows variable algorithm circles 1130 such that each circle may encompass a variable number of pixels to represent the probe encircled probe feature. A tight threshold means that the circle should tend to be drawn around the brightest group of pixels and not include dimmer pixels that could be encompassed, for example, by a larger diameter circle. An easy threshold means that the dimmer pixels should tend to be included within the circle. FIG. 11B shows fixed algorithm circles 1132, all of which are a same diameter, which may be user selected in some implementations. In this context, a tight threshold means that the circles tend to be centered around the brightest group of pixels, whereas an easy threshold means that dimmer pixels tend to be included in determining the center of the circle. As indicated by graphical element 920, user 701 may also select an estimated feature size. For instance, if the probe features are deposited using a pin, such as ones employed using the Pin-and-Ring™ technology of the Affymetrix® 417™ or 427™ Arrayers, then user 701 may select a pin size, e.g., 125 microns as shown in element 920.

Figure 10:
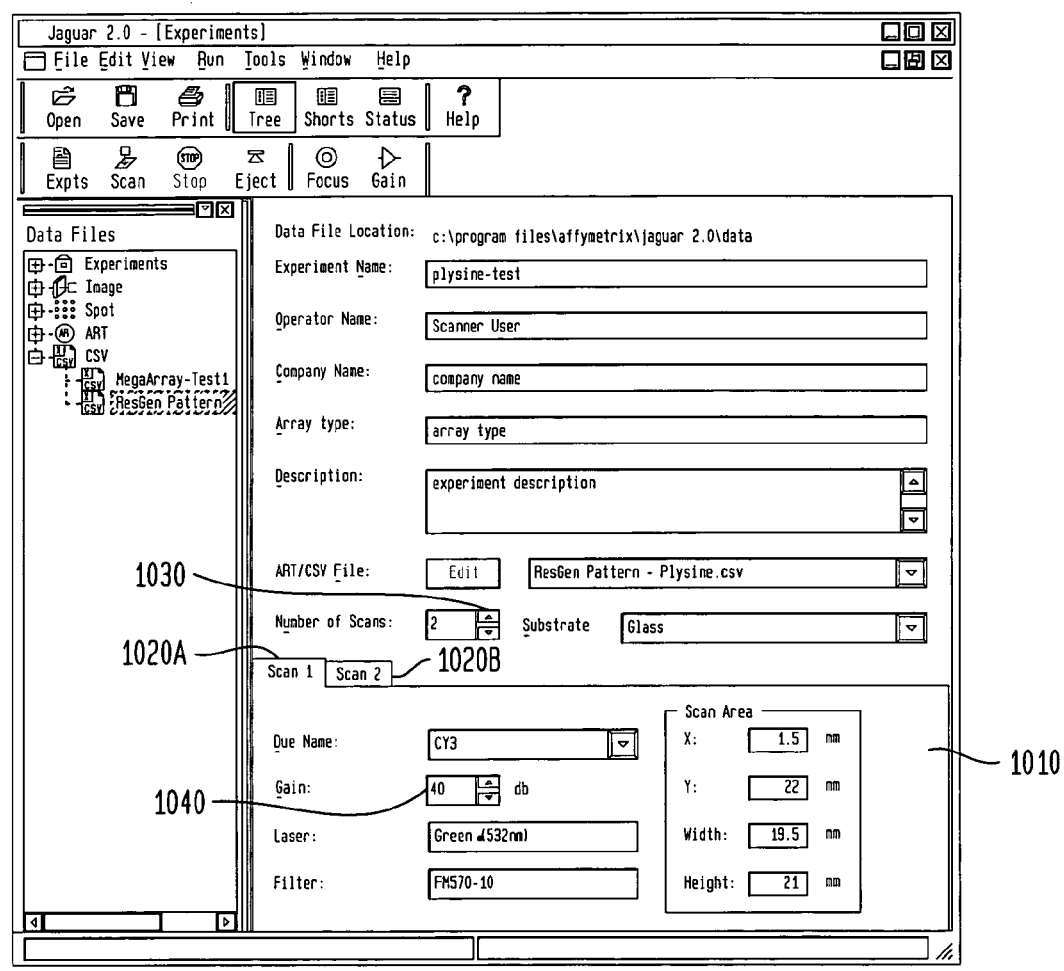
FIG. 10 is an illustrative implementation of another graphical user interface employed in cooperation with the application of FIG. 8 to receive user commands to span N number of multiple images.

It is now illustratively assumed that GUI manager 810 provides GUI 782B of FIG. 10 to user 701, also typically in response to a user selection. User 701 employs GUI 782B to select a number of images to generate by scanning (see step 1215). For example, graphical elements 1030 are provided in this example so that user 701 may enter any positive integer number (that may, of course, be limited based on practicalities of scanning, storing data, and so on) to indicate the number of images. Using tabs 1020, or other conventional techniques, user 701 may provide further options for specifying scan parameters such as the gain to be employed (see graphical element 1040).

In some implementations, each of the scans will be done on a same probe array. For example, one scan may be done using excitation source 420A and another scan may be done using excitation source 420B. Because the same probe features are scanned in both cases, they are thus generally assured to be in the same locations. Therefore, although the images generally will not be the same (since one excitation source elicits emissions of one wavelength providing one image and the other excitation source elicits emissions of another wavelength to provide another image), an alignment grid based on one of the images may be applied to the other image (or multiple other images using, for instance, multiple additional excitation sources) due to the commonality of probe feature locations. Moreover, in some implementations, the images need not be scanned from the same probe array. Rather, for example, arrayer 120 may be programmed to deposit spots in particular locations in the same pattern on multiple slides and/or on multiple spotted probe arrays on a same slide. Thus, probe feature locations thus may generally be expected to be the same, or close to the same, in the multiple spotted probe arrays. Commonality of probe feature locations also typically may be achieved with substantial precision in synthesized arrays. Thus, implementations described herein in which multiple images are described as being scanned from a same array will be understood to be illustrative and non-limiting.

In some implementations, all of the scans may be done before further processing by application 790 (see steps 1220 and 1225). However, it need not be so; rather, an image may be scanned and analyzed, then another scanned and analyzed, and so on in any sequence.

As noted, grid aligner 830 aligns a grid with a first image. Any technique for aligning a grid with an image, now available or to be developed in the future, may be employed by aligner 830. As one non-limiting example, aligner 830 may employ the techniques and methods described in U.S. patent application, Ser. No. 09/681,819, incorporated above, and/or the techniques and methods described in U.S. Pat. No. 6,090,555, hereby incorporated herein by reference in its entirety for all purposes. Examples of alignment grids superimposed on a scanned image are shown as grid 1110A of FIG. 11A and grid 1110B of FIG. 11B. Although grids 1110 of these figures are shown as consisting of horizontal and parallel lines, other grid configurations may be employed in other implementations. As noted, image analysis manager 850 includes image analyzer 852 that generates grid alignment data for a particular image, referred to as a first image or, image A, based on the alignment by grid aligner 830 of a grid with the first image (see step 1240). This alignment of a grid with image A may be initiated by a user selection of an appropriate element in an interface (see decision element 1230) or, in other implementations, it may be initiated automatically by application 790 when scanning is completed or at the occurrence of another event. It will be understood that the terms first image, or image A, are applied to distinguish this image from other images, and are not intended to limit the image to the first one scanned in time or to any other particular image. Rather, any of the N images selected by user 701 may be used as this first image or image A. Grid alignment data generated by analyzer 852 typically includes data to identify the pixels associated with each probe feature for purposes of analysis (such as gene expression analysis) and thus distinguish the pixels of one probe feature from the pixels of other probe features and from background pixels.

In the present illustrative implementation, the grid alignment data based on image A is stored by storer 855 in any appropriate file, data structure, or in accordance with other conventional techniques for storing information (see step 1245). For example, the data may be stored in an analysis data file 799 corresponding to image A, i.e., file 799A. Other analysis information, such as the distribution of pixel intensities in probe features of image A typically are also stored in, for example, records of file 799A corresponding to each of the probe features.

As noted, multiple scan alignment controller 860 retrieves the grid alignment data (e.g., from file 799A, see step 1235), which may be done automatically or responsive to a user-selected indication to align a second image (see decision element 1250). Image analyzer 852 analyzes the second image (and other of the user-selected N images) based on the retrieved grid alignment data (see steps 1255 and 1260). Image analysis data storer 855 stores the resulting analysis data in a file, appropriate data structure, or in accordance with other conventional techniques (see element 1265).

As will be evident to those skilled in the relevant art, application 790 may be loaded into system memory 720 and/or memory storage device 725 through an input device of devices 780. Alternatively, application 790 may be implemented as executable instructions stored in firmware, or a combination of firmware and software. Executable code corresponding to application 790 is referred to as scanner control application executable 790' and is shown for convenience with respect to the illustrated implementation as stored in system memory 720. However, instructions and data including executable instructions of executable 790', and data used or generated by it, may be located in or shifted among other memory devices, local or remote, as convenient for data storage, data retrieval, and/or execution. The instructions of executable 790', also called computer control logic, when executed by processor 705, enable computer 100B to perform functions of the illustrated systems. Accordingly, executable 790' may be referred to as a controller of computer 100B. More specifically, in some implementations, the present invention includes a computer program product comprising a computer usable medium having control logic (computer software program, including program code) stored therein. In various embodiments, software products may be implemented using any of a variety of programming languages, such as Visual C++ or Visual Basic from Microsoft Corporation, Java™ from Sun Microsystems, Inc., and/or other high or lower level programming languages. The control logic, when executed by processor 705, causes processor 705 to perform some of the functions of the invention, as described herein. In other embodiments, some functions of the present invention may be implemented primarily in hardware using, for example, a hardware state machine. Implementation of the hardware state machine so as to perform the functions described herein will be apparent to those skilled in the relevant arts.

Having described various embodiments and implementations of the present invention, it should be apparent to those skilled in the relevant art that the foregoing is illustrative only and not limiting, having been presented by way of example only. Many other schemes for distributing functions among the various functional elements of the illustrated embodiment are possible in accordance with the present invention. The functions of any element may be carried out in various ways in alternative embodiments. Also, the functions of several elements may, in alternative embodiments, be carried out by fewer, or a single, element.

For example, arrayer manager application 290 is described as executing on computer 100A that controls arrayer 120, and scanner control application 790 is described as executing on computer 100B that control scanner 160A. However, aspects of the invention need not be divided into these distinct functional elements. Rather, for example, applications 290 and 790 could be executed on a same computer that may, for example, control both arrayer 120 and scanner 160A. Moreover, applications 290 and 790 may be part of a same computer program product irrespective of whether they are executed on a same, or different, computers.

Similarly, operations of a particular functional element that are described separately for convenience need not be carried out separately. For example, the functions of image analyzer 852, image analysis data storer 855, and multiple scan alignment controller 860 could be performed by any one of them or by another element. The functions described with respect to analyzer 852, storer 855, and controller 860 are separated into distinct functional elements simply for convenience and clarity of illustration. Similarly, in some embodiments, any functional element may perform fewer, or different, operations than those described with respect to the illustrated embodiment. Also, functional elements shown as distinct for purposes of illustration may be incorporated within other functional elements in a particular implementation.

Also, the sequencing of functions or portions of functions generally may be altered. For example, the method steps shown in FIG. 11 generally need not be carried out in the order suggested by this figure. Among many possible examples, steps 1130 and 1140 could be combined or carried out in parallel, steps 1130 and 1140 could be carried out after steps 1125 and 1127, and so on. As another non-limiting example, user 701 could employ GUI manager 810, or another interface, to specify the number of images to be scanned (and/or other user selections described in relation to GUI 782B of FIG. 10) prior to specifying grid aligning parameters (as described in relation to GUI 782A of FIG. 9), rather than in the order illustratively described above.

In addition, it will be understood by those skilled in the relevant art that control and data flows between and among functional elements of the invention and various data structures may vary in many ways from the control and data flows described above. More particularly, intermediary functional elements (not shown) may direct control or data flows, and the functions of various elements may be combined, divided, or otherwise rearranged to allow parallel processing or for other reasons. Also, intermediate data structures or files may be used, various described data structures or files may be combined, the sequencing of functions or portions of functions generally may be altered, and so on. Numerous other embodiments, and modifications thereof, are contemplated as falling within the scope of the present invention as defined by appended claims and equivalents thereto.

What is claimed is:

1. A method comprising the steps of:
   (a) receiving one or more user-selected grid aligning parameters, wherein the user-selected grid aligning parameters includes a measure of probe feature size;
   (b) aligning a grid with a first image based, at least in part, upon the one or more user-selected grid aligning parameters;
   (c) generating grid alignment data based on the alignment of the grid with the first image;
   (d) storing the grid alignment data in memory;
   (e) retrieving the grid alignment data responsive to an indication to analyze a second image; and
   (f) analyzing the second image based on the retrieved grid alignment data.

2. The method of claim 1, wherein:
   the first image is generated by scanning a first probe array; and
   the second image is generated by scanning the first probe array.

3. The method of claim 2, wherein:
   the first image is generated by scanning the first probe array with a first excitation beam; and
   the second image is generated by scanning the first probe array with a second excitation beam.

4. The method of claim 3, wherein:
   the first excitation beam has a first wavelength; and
   the second excitation beam has a second wavelength different from the first wavelength.

5. The method of claim 2, wherein:
   the first probe array is a spotted array.

6. The method of claim 2, wherein:
   the first probe array is a synthesized array.

7. The method of claim 1, wherein:
   the user-selected grid aligning parameters include any one or more of the group consisting of a fixed algorithm shape with easy threshold, a fixed algorithm shape with tight threshold, a variable algorithm shape with easy threshold, a variable algorithm shape with tight threshold.

8. The method of claim 1, wherein:
   the measure of probe feature size includes a dimension of a depositing element.

9. The method of claim 1, further comprising the step of:
   (f) scanning a first probe array to generate the first and second images prior to performing step (a).

10. The method of claim 9, wherein:
    the first and second images are scanned sequentially.

11. The method of claim 9, wherein:
    the first and second images are scanned in parallel using two excitation beams.

12. The method of claim 1, further comprising the steps of:
    (f) retrieving the grid alignment data responsive to an indication to analyze one or more images in addition to the first and second images; and
    (g) analyzing each of the one or more additional images based on the retrieved grid alignment data.

13. The method of claim 12, further comprising the steps of:
    (h) receiving a user selection of a number of images to scan; and
    (i) scanning the user-selected number of images.

14. The method of claim 13, further comprising the step of:
    (j) receiving a user selection of one or more parameters for scanning.

15. The method of claim 14, wherein:
    the one or more parameters for scanning include a gain for one or more of the user-selected number of images.

16. The method of claim 14, wherein:
    the one or more parameters for scanning include an indicator of an excitation source for one or more of the user-selected number of images.

17. A computer program product, stored on a computer readable medium, comprising:
    (a) a GUI manager that receives one or more user-selected grid aligning parameters, wherein the user-selected grid aligning parameters include a measure of probe feature size;
    (b) a grid aligner that aligns a grid with a first image based, at least in part, upon the one or more user-selected grid aligning parameters; and
    (c) an image analysis manager comprising
        (i) an image analyzer that generates grid alignment data based on the alignment of the grid with the first image, (ii) an image analysis data storer that stores the grid alignment data in memory, and (iii) a multiple scan alignment controller that retrieves the grid alignment data responsive to an indication to analyze a second image;

wherein the image analyzer analyzes the second image based on the retrieved grid alignment data.

18. The computer program product of claim 17, wherein:
the first image is generated by scanning a first probe array; and
the second image is generated by scanning the first probe array.

19. The computer program product of claim 18, wherein:
the first image is generated by scanning the first probe array with a first excitation beam; and
the second image is generated by scanning the first probe array with a second excitation beam.

20. The computer program product of claim 19, wherein:
the first excitation beam has a first wavelength; and
the second excitation beam has a second wavelength different from the first wavelength.

21. The computer program product of claim 18, wherein:
the first probe array is a spotted array.

22. The computer program product of claim 18, wherein:
the first probe array is a synthesized array.

23. The computer program product of claim 17, wherein:
the user-selected grid aligning parameters include any one or more of the group consisting of a fixed algorithm shape with easy threshold, a fixed algorithm shape with tight threshold, a variable algorithm shape with easy threshold, a variable algorithm shape with tight threshold.

24. The computer program product of claim 17, wherein:
the measure of probe feature size includes a dimension of a depositing element.

25. A scanning system, comprising:
a scanner that scans a first probe array to generate a first image and a second image; and
a computer program product, comprising
(a) a GUI manager that receives one or more user-selected grid aligning parameters, wherein the user-selected grid aligning parameters includes a measure of probe feature size;
(b) a grid aligner that aligns a grid with the first image based, at least in part, upon the one or more user-selected grid aligning parameters; and
(c) an image analysis manager including
(i) an image analyzer chat generates grid alignment data based on the alignment of the grid with the first image,
(ii) an image analysis data storer that stores the grid alignment data in memory, and
(iii) a multiple scan alignment controller that retrieves the grid alignment data responsive to an indication to analyze the second image;
wherein the image analyzer analyzes the second image based on the retrieved grid alignment data.

26. The system of claim 25, wherein:
the first and second images are scanned sequentially.

27. The system of claim 25, wherein:
the first and second images are scanned in parallel using two excitation beams.

28. The system of claim 25, wherein:
the computer program product further includes a GUI manager that receives a user-selected number of images to scan, wherein the number is greater than one; and
the scanner scans the first probe array to generate the user-selected number of images, including the first and second images.

29. The system of claim 28, wherein:
the user-selected number of images to scan is greater than two;
the multiple scan alignment controller retrieves the grid alignment data responsive to an indication to analyze one or more images in addition to the first and second images; and
the image analyzer analyzes at least one of the one or more additional images based on the retrieved grid alignment data.

30. A scanning system, comprising:
a scanner that scans a first probe array to generate a first image and a second image;
a computer; and
a computer program product rhar, when executed on the computer, performs a method comprising the steps of:
(a) a GUI manager that receives one or more user-selected grid aligning parameters, wherein the user-selected grid aligning parameters includes a measure of probe feature size;
(b) aligning a grid with the first image based, at least in part, upon the one or more user-selected grid aligning parameters;
(c) generating grid alignment data based on the alignment of the grid wit the first image,
(d) scoring the grid alignment data in memory;
(e) retrieving the grid alignment darn responsive to an indication to analyze the second image; and
(f) analyzing the second image based on the retrieved gild alignment data.

31. A method comprising the steps of:
(a) receiving one or more user-selected grid aligning parameters, wherein the user-selected grid aligning parameters includes a measure of probe feature size;
(b) aligning a grid with a first image based, at least in part, upon the one or more user-selected grid aligning parameters;
(c) generating grid alignment data based on the alignment of the grid with the first image;
(d) storing the grid alignment data in memory;
(e) retrieving the grid alignment data responsive to an indication to analyze a second image; and
(f) analyzing the second image based on the retrieved grid alignment data;
wherein the first image is generated by scanning a first probe array and the second image is generated by scanning a second probe array different from the first probe array.

* * * * *

UNITED STATES PATENT AND TRADEMARK OFFICE
CERTIFICATE OF CORRECTION

PATENT NO. : 6,965,704 B2 Page 1 of 1
DATED : November 15, 2005
INVENTOR(S) : Shantanu V. Kauahikkar and Sangita S. Patil It is certified that error appears in the above-identified patent and that said Letters Patent is hereby corrected as shown below:

<u>Title page,</u>
Item [75], Inventors, "Sangita B. Patil" should read -- Sangita S. Patil --.

Signed and Sealed this

Twenty-first Day of March, 2006

JON W. DUDAS
*Director of the United States Patent and Trademark Office*